(12) United States Patent
Nishiguchi et al.

(10) Patent No.: US 9,371,293 B2
(45) Date of Patent: Jun. 21, 2016

(54) ISOXAZOLINE COMPOUND COMPOSITION

(71) Applicant: Sumitomo Chemical Company, Limited, Tokyo (JP)

(72) Inventors: Naonobu Nishiguchi, Takarazuka (JP); Kaori Ikari, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/519,212

(22) Filed: Oct. 21, 2014

(65) Prior Publication Data
US 2015/0119432 A1 Apr. 30, 2015

(30) Foreign Application Priority Data
Oct. 25, 2013 (JP) .................. 2013-221912

(51) Int. Cl.
| | | |
|---|---|---|
| A61K 31/42 | (2006.01) | |
| A61K 31/422 | (2006.01) | |
| A61K 31/437 | (2006.01) | |
| A01N 43/80 | (2006.01) | |
| A01N 25/10 | (2006.01) | |
| C07D 261/04 | (2006.01) | |
| A61K 9/14 | (2006.01) | |
| A61K 9/20 | (2006.01) | |

(52) U.S. Cl.
CPC .............. *C07D 261/04* (2013.01); *A01N 43/80* (2013.01); *A61K 9/146* (2013.01); *A61K 9/2054* (2013.01); *A61K 31/42* (2013.01); *A61K 31/422* (2013.01); *A61K 31/437* (2013.01)

(58) Field of Classification Search
CPC ... A61K 31/42; A61K 31/422; A61K 31/437; A01N 43/80; A01N 25/10
See application file for complete search history.

(56) References Cited

U.S. PATENT DOCUMENTS

| | | |
|---|---|---|
| 2007/0066617 A1 | 3/2007 | Mita et al. |
| 2009/0312330 A1 | 12/2009 | Mita et al. |
| 2010/0254959 A1 | 10/2010 | Lahm et al. |
| 2010/0279999 A1 | 11/2010 | Renold et al. |
| 2011/0059988 A1 | 3/2011 | Heckeroth et al. |
| 2011/0124858 A1 | 5/2011 | Iwata et al. |
| 2011/0251398 A1 | 10/2011 | Mita et al. |
| 2012/0029037 A1 | 2/2012 | Ikari |
| 2012/0029038 A1 | 2/2012 | Ikari |
| 2012/0029039 A1 | 2/2012 | Ikari |
| 2012/0029040 A1 | 2/2012 | Ikari |
| 2012/0172615 A1 | 7/2012 | Mita et al. |
| 2013/0131118 A1 | 5/2013 | Ikari |
| 2013/0217736 A1 | 8/2013 | Lahm et al. |
| 2013/0296559 A1 | 11/2013 | Mita et al. |
| 2014/0080877 A1 | 3/2014 | Renold et al. |
| 2014/0171475 A1 | 6/2014 | Ikari |

FOREIGN PATENT DOCUMENTS

| | | | |
|---|---|---|---|
| EP | 2412238 A1 | 2/2012 | |
| EP | 2412241 A1 | 2/2012 | |
| EP | 2601838 A1 | 6/2013 | |
| JP | 2003-313104 A | 11/2003 | |
| JP | 2012-046485 A | 3/2012 | |
| JP | 2012-046486 A | 3/2012 | |
| JP | 2012-046487 A | 3/2012 | |
| JP | 2012-046488 A | 3/2012 | |
| JP | 2013-173704 * | 9/2013 | ............. A61K 31/42 |
| JP | 2013-173705 * | 9/2013 | ............. A61K 31/42 |
| WO | 2012165186 A1 | 12/2012 | |

OTHER PUBLICATIONS

JP 2013-173705 English Translation Sep. 4, 2015.*
JP 2013-173704 English Translation Sep. 4, 2015.*
Extended European Search Report issued Mar. 11, 2015 in EP Application No. 14190283.3.
Sinha et al, "Solid Dispersion: An Alternaticve Technique for Bioavailability Enhancement of Poorly Soluble Drugs," Journal of Dispersion Science and Technology, vol. 30, No. 10, pp. 1458-1473 (2009).

* cited by examiner

*Primary Examiner* — Samantha Shterengarts

(74) *Attorney, Agent, or Firm* — Panitch Schwarze Belisario & Nadel LLP

(57) ABSTRACT

The present invention relates to a composition comprising an isoxazoline compound, the isoxazoline compound being dispersed in a solid vehicle of one or more polymer compounds selected from cellulose polymers and vinyl polymers.

18 Claims, 2 Drawing Sheets

ISOXAZOLINE COMPOUND COMPOSITION

BACKGROUND OF THE INVENTION

1. Field of the Invention

The present invention relates to a composition in which an isoxazoline compound is dispersed in polymer compounds and to a method for controlling an animal ectoparasite.

2. Description of the Related Art

It has been known so far to use isoxazoline compounds to control various types of pests such as parasites (so-called ectoparasites) parasitic on the body surfaces, body hairs, or positions near to these surfaces and hairs of livestock animals and pets. (See, for example, JP-A-2012-46488). It is desired to develop a composition containing an isoxazoline compound and having a more excellent control effect on ectoparasites.

PRIOR ART DOCUMENT

Patent Document

Patent Document 1: JP-A-2012-46488

SUMMARY OF THE INVENTION

It is an object of the present invention to provide an isoxazoline compound composition.

The inventors of the present invention have made earnest studies, and as a result, found that a composition prepared by dispersing an isoxazoline compound which is solid at ambient temperature and is represented by the following formula (I) in vehicle of a specific polymer compounds has an excellent control effect on animal ectoparasites, to complete the present invention.

Accordingly, the present invention is as follows:

<1> A composition comprising an isoxazoline compound represented by the following formula (I), the isoxazoline compound being dispersed in a solid vehicle of one or more polymer compounds selected from cellulose polymers and vinyl polymers:

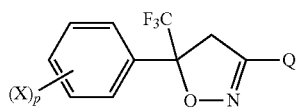

(I)

wherein X represents a halogen atom or a C1-C3 haloalkyl group,
p denotes an integer from 0 to 5; and
Q represents a group selected from the following Q1 to Q8:

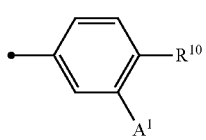

Q1

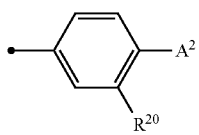

Q2

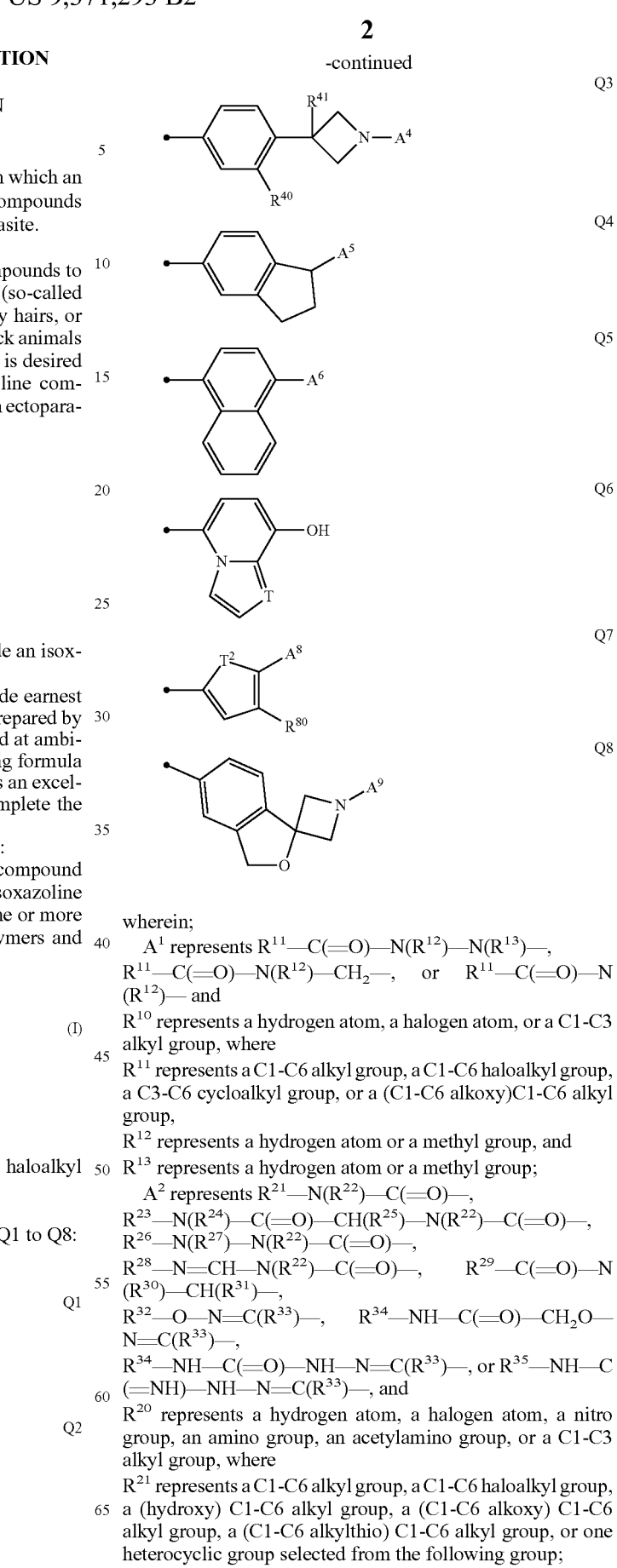

wherein;
$A^1$ represents $R^{11}$—C(=O)—N($R^{12}$)—N($R^{13}$)—, $R^{11}$—C(=O)—N($R^{12}$)—CH$_2$—, or $R^{11}$—C(=O)—N($R^{12}$)— and $R^{10}$ represents a hydrogen atom, a halogen atom, or a C1-C3 alkyl group, where $R^{11}$ represents a C1-C6 alkyl group, a C1-C6 haloalkyl group, a C3-C6 cycloalkyl group, or a (C1-C6 alkoxy)C1-C6 alkyl group, $R^{12}$ represents a hydrogen atom or a methyl group, and $R^{13}$ represents a hydrogen atom or a methyl group;

$A^2$ represents $R^{21}$—N($R^{22}$)—C(=O)—,
$R^{23}$—N($R^{24}$)—C(=O)—CH($R^{25}$)—N($R^{22}$)—C(=O)—,
$R^{26}$—N($R^{27}$)—N($R^{22}$)—C(=O)—,
$R^{28}$—N=CH—N($R^{22}$)—C(=O)—, $R^{29}$—C(=O)—N($R^{30}$)—CH($R^{31}$)—,
$R^{32}$—O—N=C($R^{33}$)—, $R^{34}$—NH—C(=O)—CH$_2$O—N=C($R^{33}$)—,
$R^{34}$—NH—C(=O)—NH—N=C($R^{33}$)—, or $R^{35}$—NH—C(=NH)—NH—N=C($R^{33}$)—, and $R^{20}$ represents a hydrogen atom, a halogen atom, a nitro group, an amino group, an acetylamino group, or a C1-C3 alkyl group, where $R^{21}$ represents a C1-C6 alkyl group, a C1-C6 haloalkyl group, a (hydroxy) C1-C6 alkyl group, a (C1-C6 alkoxy) C1-C6 alkyl group, a (C1-C6 alkylthio) C1-C6 alkyl group, or one heterocyclic group selected from the following group;

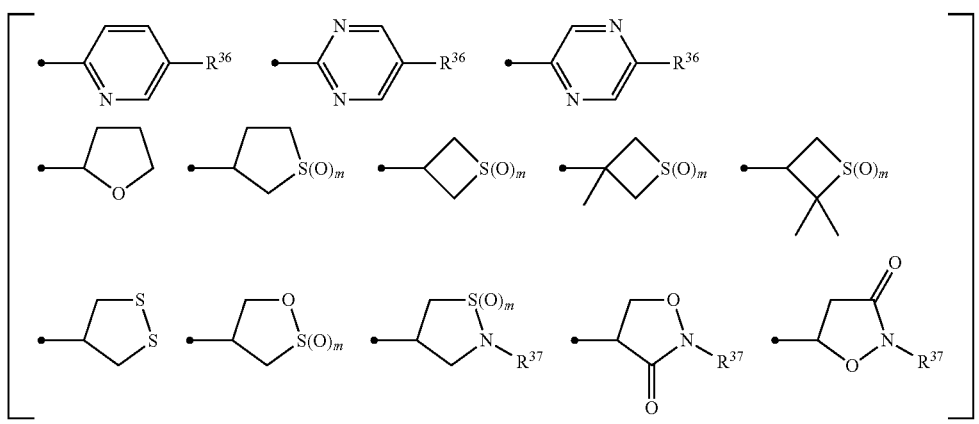

wherein m denotes a number of 0, 1 or 2, $R^{36}$ represents a hydrogen atom, a chlorine atom, or a cyano group, and $R^{37}$ represents a hydrogen atom, a C1-C6 alkyl group, or a C1-C6 haloalkyl group, $R^{22}$ represents a hydrogen atom, (C1-C6 alkyl)carbonyl group or a (C1-C6 alkoxy)carbonyl group, $R^{23}$ represents a C1-C6 alkyl group, a C1-C6 haloalkyl group, or a (C1-C6 alkoxy)C1-C6 alkyl group, $R^{24}$ represents a hydrogen atom or a C1-C3 alkyl group, $R^{25}$ represents a hydrogen atom or a C1-C3 alkyl group, $R^{26}$ represents a phenyl group, $R^{27}$ represents a hydrogen atom or a C1-C3 alkyl group, $R^{28}$ represents a C1-C3 alkoxy group, $R^{29}$ represents a C1-C6 alkyl group, a C1-C6 haloalkyl group, a C3-C6 cycloalkyl group, a (C3-C6 cycloalkyl)C1-C6 alkyl group, a (C1-C6 alkoxy)C1-C6 alkyl group, or a C1-C6 alkoxy group, $R^{30}$ represents a hydrogen atom or a C1-C3 alkyl group, $R^{31}$ represents a hydrogen atom or a C1-C3 alkyl group, $R^{32}$ represents a hydrogen atom, a C1-C6 alkyl group, or a C1-C6 haloalkyl group, $R^{33}$ represents a hydrogen atom, a cyano group, a C1-C3 alkyl group, a C1-C3 alkoxy group, or a (C1-C3 alkyl)carbonyl group, $R^{34}$ represents a C1-C6 alkyl group, a C1-C6 haloalkyl group, or a (C3-C6 cycloalkyl)C1-C6 alkyl group, and $R^{35}$ represents a hydrogen atom, a C1-C6 alkyl group, or a C1-C6 haloalkyl group;

$A^4$ represents $R^{42}$—C(=O)— or $R^{42}$—NH—C(=O)—, $R^{40}$ represents a hydrogen atom, a halogen atom, a nitro group, an amino group, an acetylamino group, or a C1-C3 alkyl group, and $R^{41}$ represents a hydrogen atom, a fluorine atom, or a hydroxyl group, where $R^{42}$ represents a C1-C6 alkyl group, a C1-C6 haloalkyl group, a cyano(C1-C3 alkyl) group, a C3-C6 cycloalkyl group, a (C1-C6 alkoxy) C1-C6 alkyl group, a (C1-C6 alkylthio) C1-C6 alkyl group, a (C1-C6 alkylsulfinyl)C1-C6 alkyl group, or a (C1-C6 alkylsulfonyl)C1-C6 alkyl group;

$A^5$ represents $R^{51}$—N($R^{52}$)—, $R^{53}$—C(=O)—N($R^{52}$)—, $R^{51}$—N($R^{52}$)—C(=O)—N($R^{52}$)—, $R^{51}$—O—C(=O)—N($R^{52}$)—, or $R^{53}$—C(=O)—, where $R^{51}$ represents a C1-C6 alkyl group, a C1-C6 haloalkyl group, or a C3-C6 cycloalkyl group, $R^{52}$ represents a hydrogen atom or a C1-C3 alkyl group, and $R^{53}$ represents a C1-C6 alkyl group, a C1-C6 haloalkyl group, a C3-C6 cycloalkyl group, a (hydroxy)C1-C6 alkyl group, or a (C1-C6 alkoxy)C1-C6 alkyl group;

$A^6$ represents $R^{61}$—N($R^{62}$)—C(=O)— or $R^{63}$—N($R^{64}$)—C(=O)—CH($R^{65}$)—N($R^{62}$)—C(=O)—, where $R^{61}$ represents a C1-C6 alkyl group, a C1-C6 haloalkyl group, a (hydroxy) C1-C6 alkyl group, a (C1-C6 alkoxy) C1-C6 alkyl group, or a (C1-C6 alkylthio)C1-C6 alkyl group, $R^{62}$ represents a hydrogen atom, a (C1-C6 alkyl)carbonyl group or a (C1-C6 alkoxy)carbonyl group, $R^{63}$ represents a C1-C6 alkyl group, a C1-C6 haloalkyl group, or a (C1-C6 alkoxy)C1-C6 alkyl group, $R^{64}$ represents a hydrogen atom or a C1-C6 alkyl group, and $R^{65}$ represents a hydrogen atom;

$A^7$ represents $R^{71}$—N($R^{72}$)—C(=O)— or $R^{73}$—N($R^{74}$)—C(=O)—CH($R^{75}$)—N($R^{72}$)—C(=O)—, and T represents a nitrogen atom or $CR^{76}$, where $R^{71}$ represents a C1-C6 alkyl group, a C1-C6 haloalkyl group, a (hydroxy) C1-C6 alkyl group, a (C1-C6 alkoxy) C1-C6 alkyl group, or a (C1-C6 alkylthio) C1-C6 alkyl group, $R^{72}$ represents a hydrogen atom, a (C1-C6 alkyl)carbonyl group, or a (C1-C6 alkoxy)carbonyl group, $R^{73}$ represents a C1-C6 alkyl group, a C1-C6 haloalkyl group, or a (C1-C6 alkoxy)C1-C6 alkyl group, $R^{74}$ represents a hydrogen atom or a C1-C6 alkyl group, $R^{75}$ represents a hydrogen atom or a C1-C6 alkyl group, and $R^{76}$ represents a hydrogen atom or a C1-C3 alkyl group;

$T^2$ represents —$CH_2$=$CH_2$—, an oxygen atom, or a sulfur atom;

$A^8$ represents $R^{11}$—C(=O)—N($R^{12}$)—N($R^{13}$)— or $R^{11}$—C(=O)—N($R^{12}$)—$CH_2$— and $R^{80}$ represents a hydrogen atom, a halogen atom, or a C1-C3 alkyl group; and $A^9$ represents $R^{92}$—C(=O)— or $R^{92}$—NH—C(=O)—, where $R^{92}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group.

<2> The composition according to <1>, wherein the ratio by weight of the isoxazoline compound to the polymer compound is 1:0.1 to 1:100.

<3> The composition according to <1> or <2>, wherein the polymer compound is one or more polymer compounds selected from the group consisting of a vinyl pyrrolidone/ vinyl acetate copolymer, polyvinyl pyrrolidone, dimethylaminoethyl methacrylate/butyl methacrylate/methyl methacrylate copolymer, hydroxypropylmethyl cellulose acetate succinate, hydroxypropylmethyl cellulose phthalate and hydroxypropylmethyl cellulose.

<4> The composition according to any one of <1> to <3>, wherein the isoxazoline compound is one or more compounds selected from compounds represented by the following formulae (II) to (V):

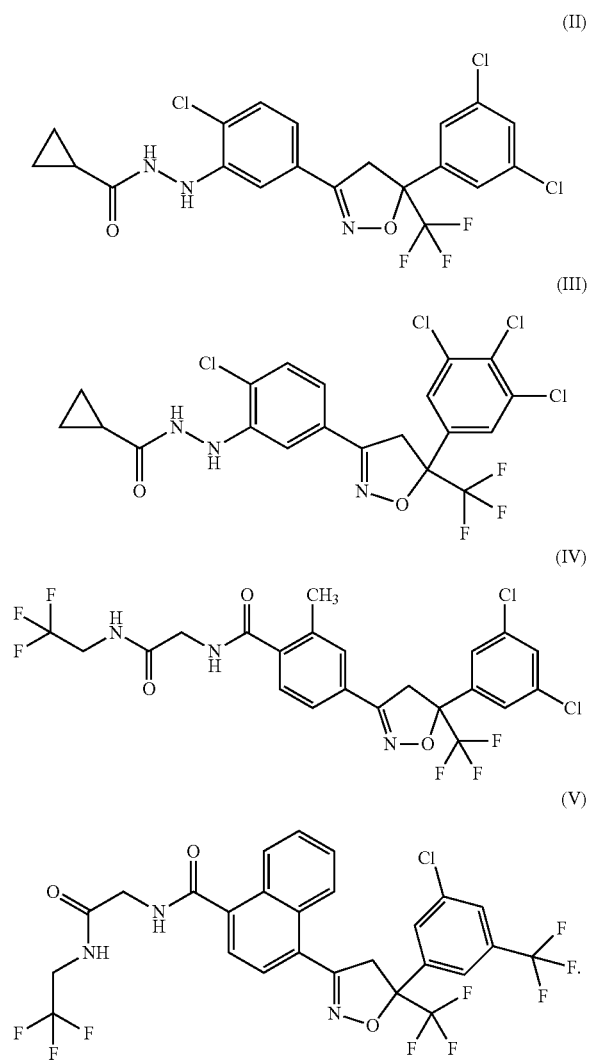

<5> An animal ectoparasiticide produced using the composition as claimed in any one of <1> to <4>.

<6> A method for controlling ectoparasites, the method comprising orally administering the composition as claimed in anyone of <1> to <4> or the animal ectoparasiticide as claimed in claim 5 to a host animal.

<7> The method for controlling ectoparasites according to <6> wherein the ectoparasite to be controlled is an ectoparasite belonging to order Siphonaptera, order Anoplura, or order Acarina.

<8> The method for controlling ectoparasites according to <6> or <7>, wherein the host animal is a livestock animal or a pet.

<9> The method for controlling ectoparasites according to any one of <6> to <8>, wherein the host animal is a dog, a cat, a horse, or a rabbit.

<10> A method for producing a composition, the method comprising a step of kneading a mixture of an isoxazoline compound represented by the formula (I) disclosed in <1> and one or more polymer compounds selected from cellulose polymers and vinyl polymers at a temperature equal to or higher than the melting point of the isoxazoline compound and equal to or higher than the temperature at which the polymer compound melts, for 3 minutes or more and a step of, then, cooling the kneaded mixture to a temperature less than the melting point of the isoxazoline compound and less than the glass transition temperature of the polymer compound.

<11> A method for producing a composition, the method comprising a step of dissolving an isoxazoline compound represented by the formula (I) disclosed in <1> and one or more polymer compounds selected from cellulose polymers and vinyl polymers in a solvent to obtain a solution and a step of distilling the solvent from the solution at a temperature less than the melting point of the isoxazoline compound and less than the glass transition temperature of the polymer compound.

According to the present invention, an isoxazoline compound composition having an excellent control effect on animal ectoparasites can be provided.

MODE FOR CARRYING OUT THE INVENTION

Figure 1:
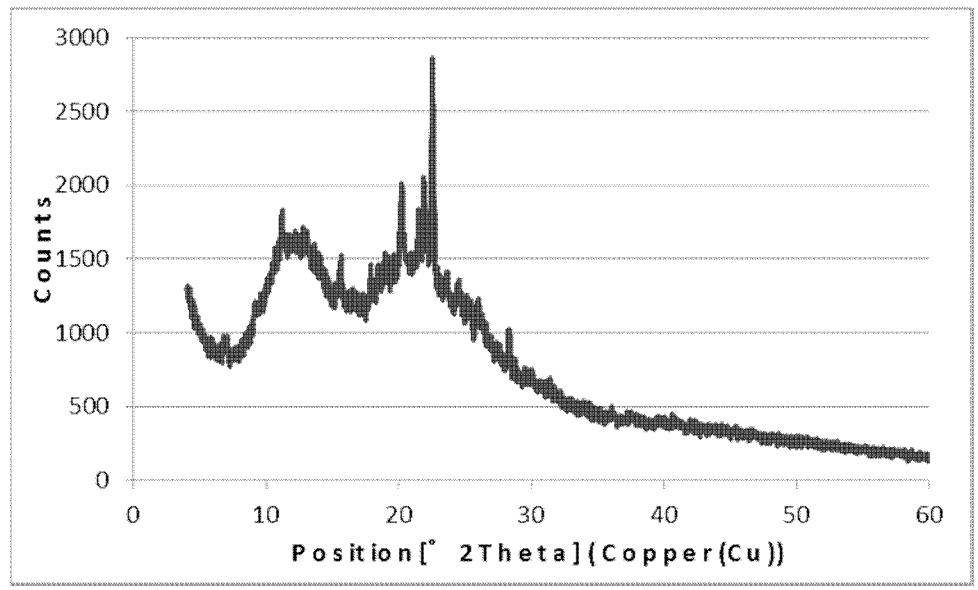
FIG. 1 is the powder X-ray diffraction of the comparison preparation 1.

A composition according to the present invention (hereinafter referred to as "the composition of the present invention") is characterized in that an isoxazoline compound which is solid at ambient temperature and is represented by the following formula (I) (hereinafter referred to as "the isoxazoline compound") is dispersed in a solid vehicle of one or more polymer compounds selected from cellulose polymers and vinyl polymers (hereinafter referred to as "the polymer compound").

In this description, the isoxazoline compound is as follows.

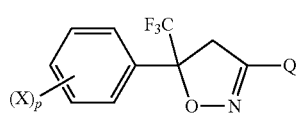

wherein X represents a halogen atom or a C1-C3 haloalkyl group,
p denotes an integer from 0 to 5; and
Q represents a group selected from the following Q1 to Q8;

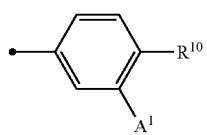

-continued

Q2
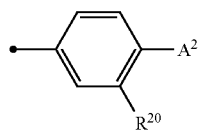

Q7
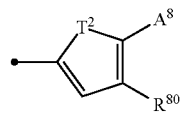

Q3
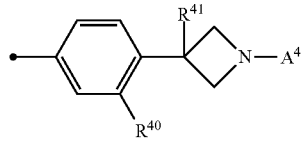

Q8
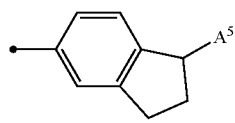

Q4
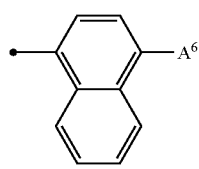

wherein;

$A^1$ represents $R^{11}$—C(=O)—N($R^{12}$)—N($R^{13}$)—, $R^{11}$—C(=O)—N($R^{12}$)—CH$_2$—, or $R^{11}$—C(=O)—N($R^{12}$)— and $R^{10}$ represents a hydrogen atom, a halogen atom, or a C1-C3 alkyl group, where $R^{11}$ represents a C1-C6 alkyl group, a C1-C6 haloalkyl group, a C3-C6 cycloalkyl group, or a (C1-C6 alkoxy)C1-C6 alkyl group, $R^{12}$ represents a hydrogen atom or a methyl group, and $R^{13}$ represents a hydrogen atom or a methyl group;

Q5

$A^2$ represents $R^{21}$—N($R^{22}$)—C(=O), $R^{23}$—N($R^{24}$)—C(=O)—CH($R^{25}$)—N($R^{22}$)—C(=O)—, $R^{26}$—N($R^{27}$)—N($R^{22}$)—C(=O)—, $R^{28}$—N=CH—N($R^{22}$)—C(=O)—, $R^{29}$—C(=O)—N($R^{30}$)—CH($R^{31}$)—, $R^{32}$—O—N=C($R^{33}$)—, $R^{34}$—NH—C(=O)—CH$_2$O—N=C($R^{33}$)—, $R^{34}$—NH—C(=O)—NH—N=C($R^{33}$)—, or $R^{35}$—NH—C(=NH)—NH—N=C($R^{33}$)—, and

Q6

$R^{20}$ represents a hydrogen atom, a halogen atom, a nitro group, an amino group, an acetylamino group, or a C1-C3 alkyl group, where $R^{21}$ represents a C1-C6 alkyl group, a C1-C6 haloalkyl group, a (hydroxy) C1-C6 alkyl group, a (C1-C6 alkoxy) C1-C6 alkyl group, a (C1-C6 alkylthio) C1-C6 alkyl group, or one heterocyclic group selected from the following group;

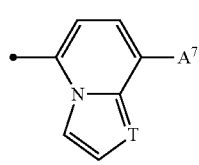

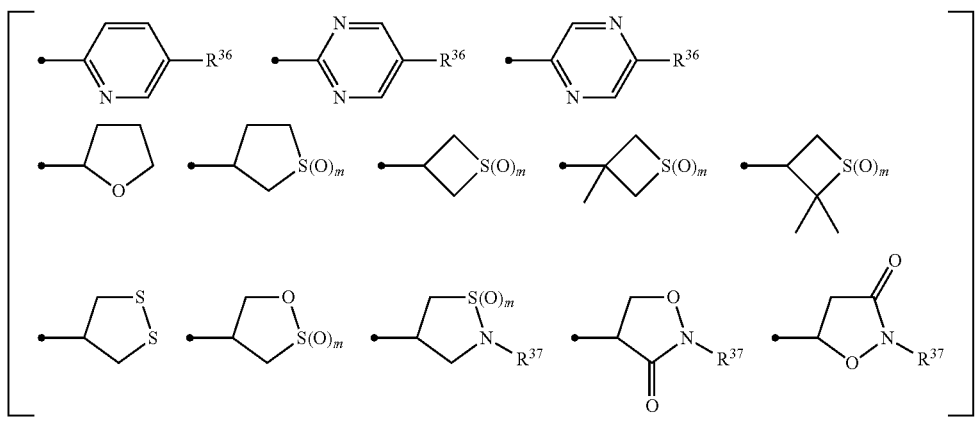

wherein m denotes a number of 0, 1 or 2, $R^{36}$ represents a hydrogen atom, a chlorine atom, or a cyano group, and $R^{37}$ represents a hydrogen atom, a C1-C6 alkyl group, or a C1-C6 haloalkyl group, $R^{22}$ represents a hydrogen atom, a (C1-C6 alkyl)carbonyl group or a (C1-C6 alkoxy)carbonyl group, $R^{23}$ represents a C1-C6 alkyl group, a C1-C6 haloalkyl group, or a (C1-C6 alkoxy)C1-C6 alkyl group, $R^{24}$ represents a hydrogen atom or a C1-C3 alkyl group, $R^{25}$ represents a hydrogen atom or a C1-C3 alkyl group, $R^{26}$ represents a phenyl group, $R^{27}$ represents a hydrogen atom or a C1-C3 alkyl group, $R^{28}$ represents a C1-C3 alkoxy group, $R^{29}$ represents a C1-C6 alkyl group, a C1-C6 haloalkyl group, a C3-C6 cycloalkyl group, a (C3-C6 cycloalkyl)C1-C6 alkyl group, a (C1-C6 alkoxy)C1-C6 alkyl group, or a C1-C6 alkoxy group, $R^{30}$ represents a hydrogen atom or a C1-C3 alkyl group, $R^{31}$ represents a hydrogen atom or a C1-C3 alkyl group, $R^{32}$ represents a hydrogen atom, a C1-C6 alkyl group, or a C1-C6 haloalkyl group, $R^{33}$ represents a hydrogen atom, a cyano group, a C1-C3 alkyl group, a C1-C3 alkoxy group, or a (C1-C3 alkyl)carbonyl group, $R^{34}$ represents a C1-C6 alkyl group, a C1-C6 haloalkyl group, or a (C3-C6 cycloalkyl)C1-C6 alkyl group, and $R^{35}$ represents a hydrogen atom, a C1-C6 alkyl group, or a C1-C6 haloalkyl group;

$A^4$ represents $R^{42}$—C(=O)— or $R^{42}$—NH—C(=O)—, $R^{40}$ represents a hydrogen atom, a halogen atom, a nitro group, an amino group, an acetylamino group, or a C1-C3 alkyl group, and $R^{41}$ represents a hydrogen atom, a fluorine atom, or a hydroxyl group, where $R^{42}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group;

$A^5$ represents $R^{51}$—N($R^{52}$)—, $R^{53}$—C(=O)—N($R^{52}$)—, $R^{51}$—N($R^{52}$)—C(=O)—N($R^{52}$)—, $R^{51}$—O—C(=O)—N($R^{52}$)—, or $R^{53}$—C(=O)—, where $R^{51}$ represents a C1-C6 alkyl group, a C1-C6 haloalkyl group, or a C3-C6 cycloalkyl group, $R^{52}$ represents a hydrogen atom or a C1-C3 alkyl group, and $R^{53}$ represents a C1-C6 alkyl group, a C1-C6 haloalkyl group, a C3-C6 cycloalkyl group, a (hydroxy)C1-C6 alkyl group, or a (C1-C6 alkoxy)C1-C6 alkyl group;

$A^6$ represents $R^{61}$—N($R^{62}$)—C(=O)— or $R^{63}$—N($R^{64}$)—C(=O)—CH($R^{65}$)—N($R^{62}$)—C(=O)—, where $R^{61}$ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio)C1-C6 alkyl group, $R^{62}$ represents a hydrogen atom, a (C1-C6 alkyl)carbonyl group or a (C1-C6 alkoxy)carbonyl group, $R^{63}$ represents a C1-C6 alkyl group, a C1-C6 haloalkyl group, or a (C1-C6 alkoxy)C1-C6 alkyl group, $R^{64}$ represents a hydrogen atom or a C1-C6 alkyl group, and $R^{65}$ represents a hydrogen atom;

$A^7$ represents $R^{71}$—N($R^{72}$)—C(=O)— or $R^{73}$—N($R^{74}$)—C(=O)—CH($R^{75}$)—N($R^{72}$)—C(=O)—, and T represents a nitrogen atom or $CR^{76}$, where $R^{71}$ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio)C1-C6 alkyl group, $R^{72}$ represents a hydrogen atom, a (C1-C6 alkyl)carbonyl group, or a (C1-C6 alkoxy)carbonyl group, $R^{73}$ represents a C1-C6 alkyl group, a C1-C6 haloalkyl group, or a (C1-C6 alkoxy)C1-C6 alkyl group, $R^{74}$ represents a hydrogen atom or a C1-C6 alkyl group, $R^{75}$ represents a hydrogen atom or a C1-C6 alkyl group, and $R^{76}$ represents a hydrogen atom or a C1-C3 alkyl group;

$T^2$ represents —$CH_2$=$CH_2$—, an oxygen atom, or a sulfur atom;

$A^8$ represents $R^{11}$—C(=O)—N($R^{12}$)—N($R^{13}$)— or $R^{11}$—C(=O)—N($R^{12}$)—$CH_2$— and $R^{80}$ represents a hydrogen atom, a halogen atom, or a C1-C3 alkyl group; and $A^9$ represents $R^{92}$—C(=O)— or $R^{92}$—NH—C(=O)—, where $R^{92}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group.

The term "halogen atom" means a fluorine atom, chlorine atom, bromine atom, or iodine atom.

The term "C1-C3 alkyl group" means a methyl group, ethyl group, propyl group, or isopropyl group.

Examples of the "C1-C6 alkyl group" include a methyl group, ethyl group, propyl group, isopropyl group, butyl group, isobutyl group, sec-butyl group, tert-butyl group, pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group, hexyl group, 1-methylpentyl group, 2-methylpentyl group, 1,1-dimethylbutyl group, and 1,3-dimethylbutyl group.

Examples of the "C1-C6 haloalkyl group" include a fluoromethyl group, difluoromethyl group, dichloromethyl group, trifluoromethyl group, chlorofluoromethyl group, bromofluoromethyl group, chlorodifluoromethyl group, bromodifluoromethyl group, 1-fluoroethyl group, 1,1-difluoroethyl group, 2,2,2-trifluoroethyl group, 1,1,2,2,2-pentafluoroethyl group, 3,3,3-trifluoropropyl group, 1,1,2,2,3,3,3-heptafluoropropyl group, 4,4,4-trifluorobutyl group, and 1,2,2,2-tetrafluoro-1-(trifluoromethyl)ethyl group.

Examples of the "C3-C6 cycloalkyl group" include a cyclopropyl group, 1-methylcyclopropyl group, 2-methylcyclopropyl group, 2,2-dimethylcyclopropyl group, cyclobutyl group, cyclopentyl group, 1-methylcyclopentyl group, 2-methylcyclopentyl group, 3-methylcyclopentyl group, and cyclohexyl group.

Examples of the "C1-C3 alkoxy group" include a methoxy group, ethoxy group, propoxy group, and isopropoxy group.

Examples of the "(hydroxy)C1-C6 alkyl group" include a 2-hydroxyethyl group, 3-hydroxypropyl group, and 6-hydroxyhexyl group.

Examples of the "(C1-C6 alkoxy) C1-C6 alkyl group" include a methoxymethyl group, 2-methoxyethyl group, 3-methoxypropyl group, ethoxymethyl group, propoxymethyl group, hexyloxymethyl group, 6-methoxyhexyl group, and 1-methoxypropyl group.

Examples of the "(C1-C6 alkylthio)C1-C6 alkyl group" include a methylthiomethyl group, 2-methylthioethyl group, 3-methylthiopropyl group, ethylthiomethyl group, propylthiomethyl group, hexylthiomethyl group, 6-methylthiohexyl group, and 1-methylthiopropyl group.

Examples of the "(C1-C6 alkyl)carbonyl group" include a methylcarbonyl group, ethylcarbonyl group, propylcarbonyl group, isopropylcarbonyl group, and hexylcarbonyl group.

Examples of the "(C1-C6 alkoxy)carbonyl group" include a methoxycarbonyl group, ethoxycarbonyl group, propoxycarbonyl group, isopropoxycarbonyl group, and hexyloxycarbonyl group.

Examples of the "C1-C3 haloalkyl group" include a trifluoromethyl group.

Examples of the "C1-C6 alkoxy group" include a methoxy group and ethoxy group.

Examples of the "(C1-C3 alkyl)carbonyl group" include an acetyl group.

Examples of the "(C3-C6 cycloalkyl)C1-C6 alkyl group" include a cyclopropylmethyl group.

Examples of the "cyano(C1-C3 alkyl) group" include a cyanomethyl group.

Examples of the "(C1-C6 alkylthio)C1-C6 alkyl group" include a methylthiomethyl group.

Examples of the "(C1-C6 alkylsulfinyl) C1-C6 alkyl group" include a methylsulfinylmethyl group.

Examples of the "(C1-C6 alkylsulfonyl) C1-C6 alkyl group" include a methylsulfonylmethyl group.

The isoxazoline compound is a known compound described in, for example, WO2010/090344, WO2005/085216, WO2009/002809, WO2009/080250, WO2010/072781, WO2007/105814, WO2011/075591, WO2012/017359, and WO2012/120399 and may be produced by production methods described in these publications.

Specific examples of the isoxazoline compound include the following compounds:

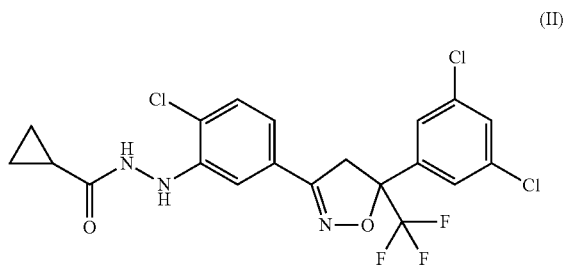

(II)

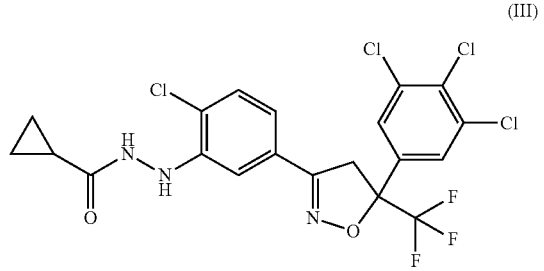

(III)

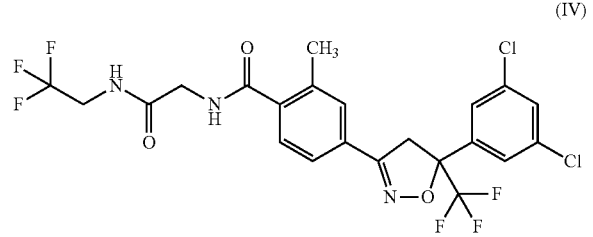

(IV)

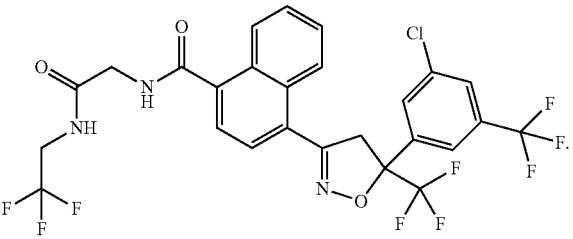

(V)

As the polymer compound in the present invention, any of commercial products and synthetic products produced by known processes may be used.

The polymer compound is one or more types selected from cellulose polymers or vinyl polymers.

The cellulose polymer means cellulose which is a carbohydrate derived from a natural polysaccharide represented by the molecular formula $(C_6H_{10}O_5)_n$ or its modified polymer. Examples of the modified polymer include polymers modified by adding reactive low-molecular compounds to some parts of hydroxyl groups in a cellulose structure.

Examples of the cellulose polymer include cellulose, microcrystalline cellulose, methyl cellulose, hydroxyethyl cellulose, hydroxyethylmethyl cellulose, hydroxypropyl cellulose, low-substituted hydroxypropyl cellulose, hydroxypropylmethyl cellulose (also called hypromellose), hydroxypropylmethyl cellulose phthalate (also called hypomellose phthalate), hydroxyethylmethyl cellulose acetate phthalate, hydroxyethyl cellulose acetate, hydroxypropylmethyl cellulose acetate, hydroxypropyl cellulose acetate succinate, hydroxyethyl cellulose acetate succinate, hydroxypropylmethyl cellulose acetate succinate, hydroxyethylmethyl cellulose acetate succinate, hydroxyethylmethyl cellulose succinate, carboxyethyl cellulose, ethylcarboxymethyl cellulose, carboxymethyl cellulose, carboxymethylethyl cellulose, cellulose acetate phthalate, methyl cellulose acetate phthalate, ethyl cellulose acetate phthalate, hydroxypropyl cellulose acetate phthalate, hydroxypropylmethyl cellulose acetate phthalate, hydroxypropyl cellulose acetate phthalate succinate, hydroxypropylmethyl cellulose acetate succinate phthalate, hydroxypropylmethyl cellulose succinate phthalate, cellulose propionate phthalate, hydroxypropyl cellulose butylate phthalate, cellulose acetate trimellitate, methyl cellulose acetate trimellitate, ethyl cellulose acetate trimellitate, hydroxypropyl cellulose acetate trimellitate, hydroxypropylmethyl cellulose acetate trimellitate, hydroxypropyl cellulose acetate trimellitate succinate, cellulose propionate trimellitate, cellulose butylate trimellitate, cellulose acetate terephthalate, cellulose acetate isophthalate, cellulose acetate pyridine carboxylate, cellulose salicylate acetate, cellulose hydroxypropylsalicylate acetate, cellulose ethylbenzoate acetate, cellulose hydroxypropylethylbenzoate acetate, cellulose ethylphthalate acetate, cellulose ethylnicotinate acetate and cellulose ethylpicolinate acetate, cellulose acetate, cellulose acetate butyrate, croscarmellose sodium, carboxymethyl cellulose calcium, and carboxymethyl cellulose sodium.

In the present invention, preferable examples of the cellulose polymer include hydroxypropylmethyl cellulose acetate succinate, hydroxypropylmethyl cellulose phthalate, and hydroxypropylmethyl cellulose.

The vinyl polymer is one of synthetic polymers obtained by polymerizing a vinyl compound (monomer) having a double bond and a synthetic polymer obtained by polymerizing a vinyl compound including the following monomers is preferable in the present invention:

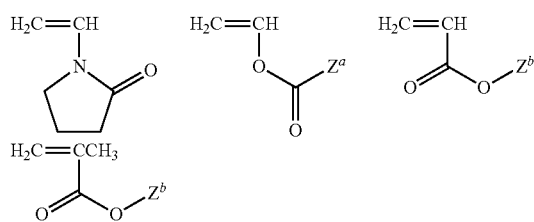

wherein Za represents a methyl group or $C_6H_4CO_2H$ and Zb represents a hydrogen atom or a methyl group.

Examples of the vinyl polymer include polyvinyl pyrrolidone, crosslinking type polyvinyl pyrrolidone, vinyl pyrrolidone/vinyl acetate copolymers, polyvinyl alcohol, polyvinyl acetate, polyvinyl acetate phthalate, polyvinyl acetal diethyl aminoacetate, crosslinking type polyacrylic acid (also called a carboxyvinyl polymer), methacrylic acid/ethylacrylate copolymers (also called a methacrylic acid copolymer LD), methacrylic acid/methylmethacrylate copolymers (also called a methacrylic acid copolymer L or methacrylic acid copolymer S), ethylacrylate/methylmethacrylate copolymers (also called a methacrylic acid copolymer NE), dimethyl aminoethyl methacrylate/butylmethacrylate/methylmethacrylate copolymers (also called an aminoalkylmethacrylate copolymer E), methacrylic acid trimethylammoniumethyl chloride/methylmethacrylate/ethylacrylate copolymers (also called an aminoalkylmethacrylate copolymer RS or aminoalkylmethacrylate copolymer RL), partially saponified products of polyvinyl acetate, ethylene glycol/propylene glycol copolymers, and ethylene/vinyl alcohol copolymers.

In the present invention, preferable examples of the vinyl polymer include polyvinyl pyrrolidone, vinyl pyrrolidone/vinyl acetate copolymers, and dimethyl aminoethyl methacrylate/butylmethacrylate/methylmethacrylate copolymers.

As the polymer compound, the above polymer compounds may be used either singly or in combination of two or more different types. The polymer compound may be either a crystalline polymer or an amorphous polymer. The polymer compound is preferably an amorphous polymer.

In the composition of the present invention, the ratio by weight of the isoxazoline compound to the polymer compound is usually 1:0.1 to 1:100, preferably 1:0.1 to 1:50, more preferably 1:0.5 to 1:9, even more preferably 1:0.5 to 1:4.

In the composition of the present invention, the isoxazoline compound is dispersed in a solid vehicle of the polymer compound. In the present invention, the description "the isoxazoline compound is dispersed in a solid vehicle of the polymer compound" is defined as follows based on the result of powder X-ray diffraction measurement of the composition.

First, measurement of powder X-ray diffraction of the composition is made.

Next, the same isoxazoline compound and polymer compound as those contained in the above composition are mixed in the same ratio by weight as that of the above composition to obtain a sample. At this time, the solid isoxazoline compound is mixed with the solid polymer compound in a solid state as it is. The obtained sample is called a simply mixed sample. Measurement of powder X-ray diffraction of the simply mixed sample is made. In the results of measurement, a diffraction peak derived from the crystal of the isoxazoline compound and/or a diffraction peak derived from the crystal of the polymer compound are observed.

Finally, the results of measurement of the composition are compared with the results of measurement of the simply mixed sample. In the results of measurement of the composition, the composition is defined as the composition of the present invention in the case where the diffraction peak derived from the crystal which is observed in the results of measurement of the simply mixed sample is not substantially confirmed or in the case where the diffraction peak area observed in the results of measurement of the composition is more reduced than the diffraction peak area observed in the results of measurement of the simply mixed sample.

The composition of the present invention is a composition obtained by dispersing the isoxazoline compound in a solid vehicle of the polymer compound. The composition of the present invention may be produced by the following process. The isoxazoline compound is melted by heating or dissolved in a solvent to obtain a liquid form in this state, the liquid form is mixed with the polymer compound and uniformed. Then, the uniformed composition is cooled or the solvent is distilled, thereby enabling production of a composition in which the isoxazoline compound is dispersed in an amorphous state or micro-particle state in the solid vehicle of the polymer compound. In the above mixing step, the polymer compound is also preferably melted or dissolved in a solvent.

The following is a detailed description for explaining a typical method for producing the composition of the present invention.

One of the typical methods for producing the composition of the present invention is a melt method involving the following steps.

(Step 1) A mixture of the isoxazoline compound and the polymer compound is kneaded using a kneader and the like at a temperature equal to or higher than the melting point of the isoxazoline compound and equal to or higher than the temperature at which the polymer compound melts, to prepare an uniform mixture. The temperature at which the polymer compound melts is the melting point of the polymer when the polymer compound is a crystalline polymer or is the glass transition temperature of the polymer when the polymer compound is an amorphous polymer. In the present invention, the kneading is usually performed at a temperature range from 100 to 250° C. and the kneading is performed for 3 min or more. (Step 2) Next, the kneaded mixture is cooled to a temperature less than the melting point of the isoxazoline compound and less than the glass transition temperature of the polymer compound. Usually, it is preferred that the mixture is quickly cooled to a temperature lower by 50° C. or more than the melting point of the isoxazoline compound. The obtained solid composition of the present invention may be milled prior to use.

The melt extrusion method which is a type of melt method is a method in which the mixture of the isoxazoline compound and the polymer compound is kneaded using a single screw or twin screw extruder. In this method, heat or pressure is applied to the mixture in the extruder to thereby melt the isoxazoline compound and the polymer compound, thereby preparing a substantially uniform mixture, which is then extruded from a screen and then cooled quickly to a temperature less than the melting point of the isoxazoline compound and less than the glass transition temperature of the polymer compound to thereby produce a composition having a fixed shape.

Another example of the typical method for producing the composition of the present invention is a solvent method involving the following steps.

(Step 1) The isoxazoline compound and the polymer compound are dissolved in an adequate solvent to prepare a uniform solution. Examples of the solvent adequate to dissolve the isoxazoline compound and the polymer compound include ketone type solvents such as acetone and methyl ethyl ketone and alcohol type solvents such as methanol, ethanol, and isopropanol and the solvent is preferably acetone, methanol, and ethanol. A solution prepared by dissolving the isoxazoline compound in a solvent may be mixed with a solution prepared by dissolving the polymer compound in a solvent to prepare a uniform solution. (Step 2) Then, a poor solvent is added to the solution at a temperature less than the melting point of the isoxazoline compound and less than the glass transition temperature of the polymer compound, or the solvent is distilled (under a reduced pressure condition according to the need) from the solution to bring a solid-form composition into existence from the solution. The obtained solid-form composition of the present invention may be dried and then, ground prior to use.

The spray drying method which is one of the solvent methods is a method for obtaining a powder composition by spraying and drying (spray dry, fluidized bed coating) a solution containing the isoxazoline compound and the polymer compound.

A preparation obtained using the aforementioned composition of the present invention is useful for controlling ectoparasites. When the preparation is produced, excipients may be used with the intention of, for example, improving disintegrability and tackiness and reducing viscosity.

The composition of the present invention and the excipients may be mixed, granulated, or molded under pressure to produce the preparation.

Examples of the dosage form of the preparation obtained using the composition of the present invention include powders, wettable powders, granules, pellets, pastes, microcapsules, capsules (for example, hard or soft gelatin capsules), tablets (for example, orally disintegrating tablets, chewable tablets, flavor tablets, sugar-coated tablets, foaming tablets, uncoated tablets or coating tablets), treat-form chewable preparations, feed compositions for animals, feed composition concentrates for animals, and feed premixes for animals. A desirable preparation is appropriately selected in administration to animals.

Preferable examples of the dosage form in the present invention are capsules, tablets, treat-form chewable preparations, and animal feed mixtures, more preferably capsules, tablets, and treat-form chewable preparations, and even more preferably tablets.

Examples of the excipients include dilluents binders, disintegrants, flavoring substances, glidants, lubricants, other auxiliaries, preservatives, stabilizers, and pH regulators. Specific examples of the excipients include the following compounds.

Examples of the dilluents include saccharides, aluminum hydroxides, calcium hydrogen phosphates, glycine, magnesium silicate, magnesium carbonate, magnesium hydroxides, magnesium oxide, synthetic aluminum silicate, synthetic hydrotalcite, sodium hydrogencarbonate, magnesium metasilicate aluminate, magnesium silicate aluminate, calcium carbonate, precipitated calcium carbonate, calcium silicate, sodium carbonate, calcium phosphate, and sodium phosphate and mixtures of these compounds.

Examples of the saccharides include monosaccharides such as glucose and fructose, oligosaccharides such as trehalose, sucrose (for example, white soft sugar), lactose (for example, lactose hydrate and anhydrous lactose), dextrin, starch (for example, corn starch, potato starch, rice starch, wheat starch, sweet potato starch, mung bean starch, tapioca starch, and their mixtures), processed starch (for example, pregelatinized starch and gelatinized starch), polysaccharides, and sugar alcohols such as mannitol, erythritol, xylitol, and sorbitol.

Examples of aluminum hydroxides include aluminum hydroxide, dried aluminum hydroxide gel, alumina magnesium hydroxide, aluminum hydroxide/magnesium carbonate mixture dry gel, aluminum hydroxide/sodium hydrogen carbonate coprecipitate, and aluminum hydroxide/magnesium carbonate/calcium carbonate coprecipitate.

Examples of calcium hydrogen phosphates include calcium hydrogen phosphate (dibasic calcium phosphate), anhydrous calcium hydrogen phosphate (anhydrous dibasic calcium phosphate), and calcium dihydrogen phosphate (monocalcium phosphate).

Examples of the binder and disintegrants include oligosaccharides, polysaccharides and their derivatives, synthetic resins, and gums.

Examples of the oligosaccharides and polysaccharides and their derivatives include α-, β-, or γ-cyclodextrin, cross-linked β-cyclodextrin polymer, cross-linked dextran, polyanionic-β-cyclodextrin, sulfobutyl ether-7-β-cyclodextrin, pullulan, hydroxyethyl starch, hydroxypropyl starch, sodium carboxymethyl starch (sodium starch glycolate), and high amylose starch, and their mixtures.

Examples of the gums include gum arabic, xanthan gum, guar gum, carrageenan, particularly gellan gum, tragacanth, gelatin, agar, dextrin, veegum, and their mixtures.

Other examples are acacia, glucomannan, agar, alginic acid or its sodium salt, propylene glycol alginate, chitosan, silicone, gum arabic powder, carnauba wax, stearyl alcohol, cetanol, shellac, gelatin, and their mixtures.

Examples of the flavoring substances include α-, β-, or γ-cyclodextrin, aspartame, stevia, acesulfame potassium, saccharides such as reduced malt sugar syrup, dipotassium glycyrrhizinate, glycyrrhizinate, monoammonium glycyrrhizinate, saccharin, saccharin sodium, saccharin calcium, sucralose, stevia, thaumatin, neotame, amino acids or their salts such as sodium aspartate, alanine, alginine, glycine, glutamine, alginine glutamate, glutamic acid hydrochloride, and sodium glutamate, organic acids such as adipic acid, ascorbic acid, citric acid, succinic acid, tartaric acid, and malic acid, daylily, triethyl citrate, taurine, tannic acid, meat powder (for example, a beef meat powder, chicken meat powder, pork meat powder, beef liver powder, chicken liver powder, and pork liver powder), powdered skim milk, animal feed, yeasts such as a bread yeast and beer yeast, and perfumes and flavors (for example, orange essence, orange oil, caramel, camphor, cinnamon oil, spearmint oil, strawberry essence, chocolate essence, cherry flavor, spruce oil, pine oil, peppermint oil, vanilla flavor, milk flavor, cheese flavor, tuna flavor, bitter essence, fruit flavor, peppermint essence, mix flavor, beef flavor, chicken flavor, pork flavor, liver flavor, mint flavor, menthol, lemon powder, lemon oil, and rose oil), and mixtures thereof.

Examples of the glidants and lubricants include hydrous silicon dioxide, light anhydrous silicic acid, heavy anhydrous silicic acid, titanium oxide, talc, kaolin clay, diatomaceous earth, bentonite, Fubasami clay, acid clay and the like, ceramic, sericite, quarts, sulfur, activated carbon, silica gel, calcium stearate, magnesium stearate, zinc stearate, stearic acid, and magnesium aluminum silicate, sodium stearyl fumarate, glyceryl behenate, sodium laueryl sulfate, magnesium lauryl sulfate, sodium oleate, DL-leucine, sucrose fatty acid ester, polyethylene glycol, propylene glycol, glycerin, polyethylene oxide, corn oil, mineral oil, hydrogenated vegetable oil, peanut oil, or castor oil, and mixtures of these compounds.

Examples of the other auxiliaries include amphoteric surfactants, anionic surfactants, and cationic surfactants. Specific examples include the following compounds.

Examples of the amphoteric surfactants include betaine type amphoteric surfactants such as lauryl betaine and stearyl betaine, imidazoline derivatives such as di-sodium N-lauryl-p-iminodipropionate, and others such as lecithin, and mixtures of these compounds.

Anionic surfactants: alkyl sulfates such as sodium lauryl sulfate and triethanolamine lauryl sulfate, polyoxyethylene alkyl ether sulfates such as sodium polyoxyethylene lauryl ether sulfate and polyoxyethylene lauryl ether sulfate triethanolamine, alkyl benzene sulfonates such as sodium dodecylbenzenesulfonate, polyoxyethylene alkyl ether phosphates such as sodium dipolyoxyethylene lauryl ether phosphate and sodium dipolyoxyethylene oleyl ether phosphate, taurocholic acid, and sodium taurocholate.

Examples of the cationic surfactants include alkylammonium salts such as cetyltrimethylammonium chloride and distearyldimethylammonium chloride, and mixtures of these compounds.

Examples of the preservatives and stabilizers include α-tocopherol, ascorbic acid palmitate, sodium ascorbate, sodium metabisulfate, n-propyl gallate, butylated hydroxyanisole, butylated hydroxytoluene, monothioglycerol, benzalkonium chloride, benzethonium chloride, benzoic acid, benzyl alcohol, bronopol, cetrimide, chlorhexidine, chlorobutanol, chlorocresol, cresol, ethylparaben, imide urea, methylparaben, phenol, phenoxyethanol, phenylethyl alcohol, phenylmercury acetate, phenylmercury borate, phenylmercury nitrate, potassium sorbitate, sodium benzoate, sodium propionate, fumaric acid, sorbic acid, thimerosal, propylparaben, butylparaben, picolinium myristyl γ-chloride, quaternary ammonium compound, food dyes such as Food Red No. 3, Food Yellow No. 5, and Food Blue No. 1, yellow iron sesquioxide, iron sesquioxide, brown iron oxide, black iron oxide, copper chlorophyll, sodium copper chlorophyll, riboflavin, powdered green tea, dyes, aluminum, lake, caramel, colorants using iron oxide as the base, titanium dioxide, and mixtures of these compounds.

Examples of the pH regulator include organic acids, inorganic acids, and their slats. Specific examples of the pH regulator include the following compounds:

Sulfuric acid/sulfate, phosphoric acid/phosphate, acetic acid/acetate, malic acid/malate, citric acid/citrate, tartaric acid/tartrate, lactic acid/lactate, glycine/glycinate, succinic acid/succinate, maleic acid/maleate, fumaric acid/fumarate, cholic acid/cholate, pamoic acid/pamoate, mucic acid/mucicate, glutamic acid/glutamate, camphoric acid/camphorate, glutaric acid/glutarate, glycolic acid/glycolate, phthalic acid/phthalate, formic acid/formate, lauric acid/laurate, stearic acid/stearate, salicylic acid/salicylate, methanesulfonic acid/metasulfonate, benzene sulfonic acid/benzene sulfonate, sorbic acid/sorbate, picric acid/picrate, benzoic acid/benzoate, cinnamic acid/cinnamate, carbonic acid/carbonate, amino acid/amino acid salt, tris(hydroxymethyl)aminomethane, ascorbic acid/ascorbate, isoascorbic acid/isoascorbate, toluenesulfonic acid/toluene sulfonate, methanesulfonic acid/methane sulfonate, ethanesulfonic acid/ethane sulfonate, phosphonic acid/phosphonate, orthophosphoric acid/orthophosphate, hydrochloric acid/hydrochloride, sulfonic acid/sulfonate, nitric acid/nitrate, polyphosphoric acid/polyphosphate, polyvinylsulfuric acid/polyvinyl sulfate, polyvinylsulfonic acid/polyvinyl sulfonate, oxalic acid/oxalate, adipic acid/adipate, creatinine hydrochloride, pyridoxine hydrochloride, thiamine hydrochloride, cysteine hydrochloride, glycine hydrochloride, cystine dihydrochloride, peptide, sodium metabisulfite, potassium dihydrogen phosphate, and mixtures of these compounds.

The composition of the present invention may contain other insecticides, acaricides, parasiticides, and repellents, and may be combined with these agents. Examples of insecticides, acaricides, ectoparasiticidess, and repellents are explained below.

Examples of insecticide and acaricide include:

(1) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb and the like;

(2) Pyrethroid Compounds acrinathrin, alfa-cypermethrin, allethrin, benfluthrin, beta-cyfluthrin, bifenthrin, cycloprothrin, cyfluthrin, cyphenothrin, cyhalothrin, cypermethrin, deltamethrin, esfenvalerate, etofenprox, fenpropathrin, fenvalerate, flucythrinate, flufenoprox, flumethrin, fluvalinate, halfenprox, imiprothrin, permethrin, phenothrin, prallethrin, pyrethrins, resmethrin, sigma-cypermethrin, silafluofen, tefluthrin, tralomethrin, transfluthrin, metofluthrin, profluthrin, dimefluthrin, 4-methoxymethyl-2,3,5,6-tetrafluorobenzyl=3-(2-cyano-1-prop enyl)-2,2-dimethylcyclopropanecarboxylate and the like;

(3) Nereis Toxin Compounds cartap, bensultap, thiocyclam, monosultap, bisultap and the like;

(4) Neonicotinoide Compounds imidacloprid, nitenpyram, acetamiprid, thiamethoxam, thiacloprid, dinotefuran, clothianidin and the like;

(5) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron and the like;

(6) Phenyl Pyrazole Compounds acetoprole, ethiprole, fipronil, vaniliprole, pyriprole, pyrafluprole and the like;

(7) Hydrazine Compounds chromafenozide, halofenozide, methoxyfenozide, tebufenozide and the like;

(8) Macrocyclic Lactone (Macrolide) Compounds avermectin, milbemycin, ivermectin, doramectin, moxidectin, selamectin, emamectin, eprinomectin, milbemectin, abamectin, lepimectin, milbemycin oxime, nemadectin, spinosad, spinetoram;

(9) Other Insecticides machine oil, nicotine-sulfate; bromopropylate, buprofezin, chlorphenapyr, cyromazine, D-D(1,3-Dichloropropene), flupyrazofos, hydroprene, indoxacarb, metoxadiazone, pymetrozine, pyridalyl, pyriproxyfen, methoprene, sulfluramid, tolfenpyrad, triazamate, flubendiamide, cyflumetofen, Arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, nidinotefuran, potassium oleate, protrifenbute, spiromesifen, Sulfur, metaflumizone, spirotetramat, chlorantraniliprole, cyantraniliprole and the like.

Examples of Acaricides acequinocyl, amitraz, benzoximate, bromopropylate, chinomethionat, chlorobenzilate, CPCBS(chlorfenson), clofentezine, kelthane (dicofol), etoxazole, fenbutatin oxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, amidoflumet, bifenazate, cyflumetofen and the like.

Examples of Parasiticides.

pyrantel pamoate, oxantel, morantel, Praziquantel, Closantel, albendazole, cambendazole, fenbendazole, flubendazole, mebendazole, oxfendazole, oxibendazole, parbendazole, triclabendazole, levamisol, tetramisole, mebendazole, omphalotin, abamectin, ivermectin, moxidectin, doramectin, milbemectin, milbemycin oxime, emodepside, toltrazuril and the like.

Examples of Repellents

DEET (N,N-diethyl-m-toluamide), KBR3023 (N-butyl-2-oxycarbonyl-(2-hydroxy)-piperidine), cymiazol=N,-2,3-dihydro-3-methyl-1,3-thiazol-2-ylidene-2,4-xylidene, and the like.

Examples of the animal ectoparasites to be controlled by the controlling agent of the present invention include as follows:

Examples of animal ectoparasites include pests belonging to order Siphonaptera: Pulexes spp. such as *Pulex irritans*, *Ctenocephalides* spp. such as *Ctenocephalides felis* and *Ctenocephalides canis*, *Xenopsylla* spp. such as *Xenopsylla cheopis*, *Tunga* spp. such as *Tunga penetrans*, *Echidnophaga* spp. such as *Echidnophaga gallinacea*, *Nosopsyllus* spp. such as *Nosopsyllus fasciatus*, and the like.

Pests belonging to order Anoplura: *Pediculus* spp. such as *Pediculus humanus capitis*, *Phtirus* spp. such as *Pthirus pubis*, *Haematopinus* spp. such as *Haematopinus eurysternus* and *Haematopinus suis*, *Damalinia* spp. such as *Dalmalinia ovis* and *Damalinia bovis*, *Linognathus* spp. such as *Linognathus vituli* and *Linognathus ovillus*, *Solenopotes* spp. such as *Solenopotes capillatus*, and the like.

Pests belonging to order Mallophaga: *Menopon* spp. such as *Menopon gallinae*, *Trimenopon* spp., *Trinoton* spp., *Trichodectes* spp. such as *Trichodectes canis*, *Felicola* spp. such as *Felicola subrostratus*, *Bovicola* spp. such as *Bovicola bovis*, *Menacanthus* spp. such as *Menacanthus stramineus*, *Werneckiella* spp., *Lepikentron* spp. and the like.

Pests belonging to order Hemiptera: *Cimix* spp. such as *Cimex lectularius* and *Cimex hemipterus*, *Reduvius* spp. such as *Reduvius senilis*, *Arilus* spp. such as *Arilus critatus*, *Rhodnius* spp. such as *Rhodnius prolixus*, *Triatoma* spp. such as *Triatoma rubrofasciata*, *Panstrongylus* ssp. and the like.

Pests belonging to order Acarina: *Amblyomma* spp. such as *Amblyomma americanum* and *Ambryomma maculatum*, *Boophilus* spp. such as *Boophilus microplus* and *Boophilus annulatus*, *Dermacentor* spp. such as *Dermacentor variabilis*, *Dermacentor taiwanicus*, *Dermacentor reticulatus* and *Dermacentor andersoni*, *Haemaphysalis* spp. such as *Haemaphysalis longicornis*, *Haemaphysalis flava* and *Haemaphysalis campanulata*, *Ixodes* spp. such as *Ixodes ovatus*, *Ixodes persulcatus*, *Ixodes scapularis*, *Ixodes pacificus*, *Ixodes ricinus* and *Ixodes holocyclus*, *Rhipicephalus* spp. such as *Rhipicephalus sanguineus* and *Rhipicephalus appendiculatus*, *Argas* spp. such as *Argas persicus*, *Ornithodorus* spp. such as *Ornithodorus hermsi* and *Ornithodorus turicata*, *Psoroptes* spp. such as *Psoroptes ovis* and *Psoroptes equi*, *Knemidocoptes* spp. such as *Knemidocoptes mutans*, *Notoedres* spp. such as *Notoedres cati* and *Notoedres muris*, *Sarcoptes* spp. such as *Sarcoptes scabiei*, *Otodectes* spp. such as *Octodectes cynotis*, *Listrophorus* spp. such as *Listrophorus gibbus*, *Chorioptes* spp., *Hypodectes* spp., *Pterolichus* spp., *Cytodites* spp., *Laminosioptes* spp., *Dermanyssus* spp. such as *Dermanyssus gallinae*, *Ornithonyssus* spp. such as *Ornithonyssus sylviarum* and *Ornithonyssus bacoti*, *Varroa* spp. such as *Varroa jacobsoni*, *Cheyletiella* spp. such as *Cheyletiella yasguri* and *Cheyletiella blakei*, *Ornithocheyletia* spp., *Demodex* spp. such as *Demodex canis* and *Demodex cati*, *Myobia* spp., *Psorergates* spp., *Trombicula* spp. such as *Trombiculaakamushi*, *Trombiculapallida* and *Trombicula scutellaris*, and the like.

Preferable examples include pests belonging to order Siphonaptera, order Anoplura, and Acarina.

Examples of host animals which are administration targets of the composition of the present invention include animals which can be hosts of the aforementioned animal ectoparasites and generally include homoiothermal animals and cold-blooded animals raised as livestock animals or pets. Examples of the homoiothermal animals include a cow, buffalo, sheep, goat, pig, camel, deer, fallow deer, reindeer, horse, donkey, dog, cat, rabbit, ferret, mouse, rat, hamster, squirrel, monkey, mink, chinchilla, and common raccoon as mammals, and chicken, goose, turkey, duck, pigeon, parrot, and quail as birds. Examples of the cold-blooded animals include a tortoise, sea turtle, terrapin, baby spotted turtle, lizard, iguana, chameleon, gecko, rock snake, colubrid snake, and cobra. Preferable examples are homoiothermal animals and more preferable examples are mammals such as a dog, cat, cow, horse, pig, sheep, goat, and rabbit, in which a dog, cat, horse, and rabbit are even more preferable.

The method for controlling ectoparasites according to the present invention (hereinafter referred to as the control method of the present invention) is performed by orally administering the composition of the present invention in an effective dose to an animal. As examples of the target animals, the aforementioned ones are given in which livestock animals and pets are preferable.

According to the control method of the present invention, the composition of the present invention can control ectoparasites of animals therapeutically, inhibitorily, preventively, and protectively.

The composition of the present invention is administered to an animal in a dose of usually 0.01 to 5000 mg, preferably 0.1 to 100 mg, and more preferably 0.5 to 40 mg as the amount of the isoxazoline compound per 1 kg of the live weight of a target animal though it may be changed depending on the target animal or an ectoparasite to be controlled.

EXAMPLES

The present invention will be explained in more detail by way of preparation examples and test examples, which are, however, not intended to be limiting of the present invention.

It is to be noted that the isoxazoline compounds used in the following preparation examples and test examples are the following compounds. The melting point of each compound was measured three times by using a Melting Point M565 (manufactured by BUCHI) and the average of the measured three melting points was defined as the melting point of the compound.

Isoxazoline compound (II): (Melting point: 172.5° C.)

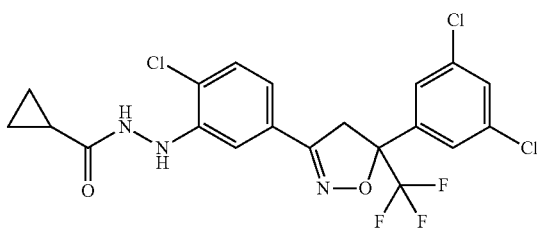 [SMILES: O=C(NNc1cc(C2=NOC(c3cc(Cl)cc(Cl)c3)(C(F)(F)F)C2)ccc1Cl)C1CC1]

Isoxazoline compound (III): (Melting point: 222.1° C.)

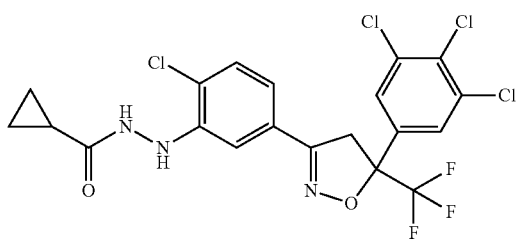 [SMILES: O=C(NNc1cc(C2=NOC(c3cc(Cl)c(Cl)c(Cl)c3)(C(F)(F)F)C2)ccc1Cl)C1CC1]

Isoxazoline compound (IV): (Melting point: 170.9° C.)

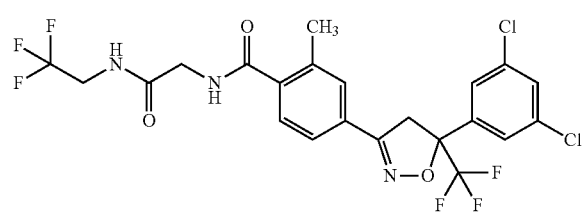 [SMILES: Cc1cc(C2=NOC(c3cc(Cl)cc(Cl)c3)(C(F)(F)F)C2)ccc1C(=O)NCC(=O)NCC(F)(F)F]

Isoxazoline compound (V): (Melting point: 100.2° C.)

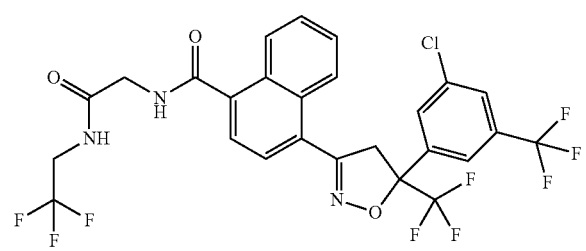 [SMILES: O=C(CNC(=O)c1ccc(C2=NOC(c3cc(Cl)cc(C(F)(F)F)c3)(C(F)(F)F)C2)c2ccccc12)NCC(F)(F)F]

Preparation Example 1

20 parts by weight of the isoxazoline compound (II) and 80 parts by weight of a vinyl pyrrolidone/vinyl acetate copolymer (trade name: Plasdone S-630, manufactured by ISP Japan Ltd., glass transition temperature: 106° C.) were mixed with each other and the mixture was kneaded under heating at 180° C. for 3 min by using a Brabender Plastograph (manufactured by Brabender GmbH & Co. KG; test kneader). The kneaded mixture was taken out, rapidly cooled by a desktop test press (manufactured by SHINTO Metal Industries Corporation) cooled to ambient temperature, and then, roughly milled by a centrifugal mill to obtain a composition (hereinafter referred to as a composition A).

Preparation Example 2

20 parts by weight of the isoxazoline compound (II) and 80 parts by weight of polyvinyl pyrrolidone (trade name: Plasdone K29/32, manufactured by ISP Japan Ltd., glass transition temperature: 160 to 170° C.) were mixed with each other and the mixture was kneaded under heating at 190° C. for 3 min by using a Brabender Plastograph (manufactured by Brabender GmbH & Co. KG; test kneader). The kneaded mixture was taken out, rapidly cooled by a desktop test press (manufactured by SHINTO Metal Industries Corporation) cooled to ambient temperature, and then, roughly milled by a centrifugal mill to obtain a composition (hereinafter referred to as a composition B).

Preparation Example 3

20 parts by weight of the isoxazoline compound (II) and 80 parts by weight of an aminoalkylmethacrylate copolymer E (trade name: EUDRAGIT E100, manufactured by Evonik Degussa Japan Co., Ltd., glass transition temperature: 48° C.) were mixed with each other and the mixture was kneaded under heating at 180° C. for 3 min by using a Brabender Plastograph (manufactured by Brabender GmbH & Co. KG; test kneader). The mixture was taken out, rapidly cooled by a desktop test press (manufactured by SHINTO Metal Industries Corporation) cooled to ambient temperature, and then, roughly milled by a centrifugal mill to obtain a composition (hereinafter referred to as a composition C).

Preparation Example 4

20 parts by weight of the isoxazoline compound (II) and 80 parts by weight of hydroxypropylmethyl cellulose acetate succinate (trade name: AQOAT AS-MG, manufactured by Shin-Etsu Chemical Co., Ltd., glass transition temperature: 120 to 135° C.) were mixed with each other and the mixture was kneaded under heating at 190° C. for 3 min by using a Brabender Plastograph (manufactured by Brabender GmbH & Co. KG; test kneader). The kneaded mixture was taken out, rapidly cooled by a desktop test press (manufactured by SHINTO Metal Industries Corporation) cooled to ambient temperature, and then, roughly milled by a centrifugal mill to obtain a composition (hereinafter referred to as a composition D).

Preparation Example 5

20 parts by weight of the isoxazoline compound (II) and 80 parts by weight of hypromellose phthalate (trade name: HPMCP HP-50, manufactured by Shin-Etsu Chemical Co., Ltd., glass transition temperature: 145 to 150° C.) were mixed with each other and the mixture was kneaded under heating at 210° C. for 3 min by using a Brabender Plastograph (manufactured by Brabender GmbH & Co. KG; test kneader). The kneaded mixture was taken out, rapidly cooled by a desktop test press (manufactured by SHINTO Metal Industries Corporation) cooled to ambient temperature, and then, roughly milled by a centrifugal mill to obtain a composition (hereinafter referred to as a composition E).

Preparation Example 6

20 parts by weight of the isoxazoline compound (II) and 80 parts by weight of hydroxypropylmethyl cellulose (trade name: TC-5R, manufactured by Shin-Etsu Chemical Co., Ltd., glass transition temperature: 170 to 210° C.) were mixed with each other and the mixture was kneaded under heating at 210° C. for 3 min by using a Brabender Plastograph (manufactured by Brabender GmbH & Co. KG; test kneader). The kneaded mixture was taken out, rapidly cooled by a desktop test press (manufactured by SHINTO Metal Industries Corporation) cooled to ambient temperature, and then, roughly milled by a centrifugal mill to obtain a composition (hereinafter referred to as a composition F).

Preparation Example 7

A mixture of 20 parts by weight of the isoxazoline compound (II) and 80 parts by weight of a vinyl pyrrolidone/vinyl acetate copolymer (trade name: Plasdone S-630, manufactured by ISP Japan Ltd., glass transition temperature: 106° C.)

was dissolved in 150 parts by weight of acetone. Acetone was distilled from the solution at ambient temperature by an evaporator to obtain a solid product as a residue. Then, the solid product was dried at ambient temperature under reduced pressure overnight. The dried solid product was roughly milled by a centrifugal mill to obtain a composition (hereinafter referred to as a composition G).

Preparation Example 8

A mixture of 20 parts by weight of the isoxazoline compound (II) and 30 parts by weight of a vinyl pyrrolidone/vinyl acetate copolymer (trade name: Plasdone S-630, manufactured by ISP Japan Ltd., glass transition temperature: 106° C.) was dissolved in 150 parts by weight of acetone. Acetone was distilled from the solution at ambient temperature by an evaporator to obtain a solid product as a residue. Then, the solid product was dried at ambient temperature under reduced pressure overnight. The dried solid product was roughly milled by a centrifugal mill to obtain a composition (hereinafter referred to as a composition H).

Preparation Example 9

A mixture of 20 parts by weight of the isoxazoline compound (II) and 30 parts by weight of a vinyl pyrrolidone/vinyl acetate copolymer (trade name: Plasdone S-630, manufactured by ISP Japan Ltd., glass transition temperature: 106° C.) was dissolved in 300 parts by weight of ethanol. Ethanol was distilled from the solution at ambient temperature by an evaporator to obtain a solid product as a residue. Then, the solid product was dried at ambient temperature under reduced pressure overnight. The dried solid product was roughly milled by a centrifugal mill to obtain a composition (hereinafter referred to as a composition I).

Preparation Example 10

A mixture of 20 parts by weight of the isoxazoline compound (II) and 80 parts by weight of polyvinyl pyrrolidone (trade name: Plasdone K29/32, manufactured by ISP Japan Ltd., glass transition temperature: 160 to 170° C.) was dissolved in 250 parts by weight of ethanol. Ethanol was distilled from the solution at ambient temperature by an evaporator to obtain a solid product as a residue. Then, the solid product was dried at ambient temperature under reduced pressure overnight. The dried solid product was roughly milled by a centrifugal mill to obtain a composition (hereinafter referred to as a composition J).

Preparation Example 11

A mixture of 20 parts by weight of the isoxazoline compound (II) and 30 parts by weight of polyvinyl pyrrolidone (trade name: Plasdone K29/32, manufactured by ISP Japan Ltd., glass transition temperature: 160 to 170° C.) was dissolved in 250 parts by weight of ethanol. Ethanol was distilled from the solution at ambient temperature by an evaporator to obtain a solid product as a residue. Then, the solid product was dried at ambient temperature under reduced pressure overnight. The dried solid product was roughly milled by a centrifugal mill to obtain a composition (hereinafter referred to as a composition K).

Preparation Example 12

A mixture of 20 parts by weight of the isoxazoline compound (II) and 80 parts by weight of an aminoalkylmethacrylate copolymer E (trade name: EUDRAGIT E100, manufactured by Evonik Degussa Japan Co., Ltd., glass transition temperature: 48° C.) was dissolved in 150 parts by weight of acetone. Acetone was distilled from the solution at ambient temperature by an evaporator to obtain a solid product as a residue. Then, the solid product was dried at ambient temperature under reduced pressure overnight. The dried solid product was roughly milled by a centrifugal mill to obtain a composition (hereinafter referred to as a composition L).

Preparation Example 13

A mixture of 20 parts by weight of the isoxazoline compound (II) and 30 parts by weight of an aminoalkylmethacrylate copolymer E (trade name: EUDRAGIT E100, manufactured by Evonik Degussa Japan Co., Ltd., glass transition temperature: 48° C.) was dissolved in 300 parts by weight of acetone to obtain a solution. Acetone was distilled from the solution at ambient temperature by an evaporator to obtain a solid product. Then, the solid product was dried at ambient temperature under reduced pressure overnight. The dried solid product was roughly milled by a centrifugal mill to obtain a composition (hereinafter referred to as a composition M).

Preparation Example 14

A mixture of 20 parts by weight of the isoxazoline compound (II) and 30 parts by weight of hydroxypropylmethyl cellulose acetate succinate (trade name: AQOAT-AS-MG, manufactured by Shin-Etsu Chemical Co., Ltd., glass transition temperature: 120 to 135° C.) was dissolved in 150 parts by weight of acetone to obtain a solution. Acetone was distilled from the solution at ambient temperature by an evaporator to obtain a solid product. Then, the solid product was dried at ambient temperature under reduced pressure overnight. The dried solid product was roughly milled by a centrifugal mill to obtain a composition (hereinafter referred to as a composition N).

Preparation Example 15

A mixture of 20 parts by weight of the isoxazoline compound (II) and 30 parts by weight of hypromellose phthalate (trade name: HPMCP HP-50, manufactured by Shin-Etsu Chemical Co., Ltd., glass transition temperature: 145 to 150° C.) was dissolved in 250 parts by weight of a mixture solvent of acetone:methanol=1.1:1 to obtain a solution. The solvent was distilled from the solution at ambient temperature by an evaporator to obtain a solid product. Then, the solid product was dried at ambient temperature under reduced pressure overnight. The dried solid product was roughly milled by a centrifugal mill to obtain a composition (hereinafter referred to as a composition O).

Preparation Example 16

55 parts by weight of the isoxazoline compound (II) and 5.5 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition P).

Preparation Example 17

40 parts by weight of the isoxazoline compound (II) and 20 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition Q).

Preparation Example 18

30 parts by weight of the isoxazoline compound (II) and 30 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition R).

Preparation Example 19

20 parts by weight of the isoxazoline compound (II) and 40 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition S).

Preparation Example 20

A mixture of 2 parts by weight of the isoxazoline compound (II) and 8 parts by weight of hydroxypropylmethyl cellulose (trade name: TC-5R, manufactured by Shin-Etsu Chemical Co., Ltd., glass transition temperature: 170 to 210° C.) was dissolved in 250 parts by weight of acetone to obtain a solution. The solvent was distilled from the solution at ambient temperature by an evaporator to obtain a solid product. Then, the solid product was dried at ambient temperature under reduced pressure overnight. The dried solid product was roughly milled by a centrifugal mill to obtain a composition (hereinafter referred to as a composition T).

Preparation Example 21

20 parts by weight of the isoxazoline compound (III) and 80 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition U).

Preparation Example 22

20 parts by weight of the isoxazoline compound (IV) and 80 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition V).

Preparation Example 23

20 parts by weight of the isoxazoline compound (V) and 80 parts by weight of vinyl pyrrolidone/vinyl acetate copolymer (trade name: Plasdone S-630, manufactured by ISP Japan Ltd., glass transition temperature: 106° C.) were mixed and the mixture was kneaded under heating at 180° C. for 3 min by using a Brabender Plastograph (manufactured by Brabender GmbH & Co. KG; test kneader). The kneaded mixture was taken out, quickly cooled by a desktop test press (manufactured by SHINTO Metal Industries Corporation) cooled to ambient temperature, and then, roughly milled by a centrifugal mill to obtain a composition (hereinafter referred to as a composition W).

Preparation Example 24

The isoxazoline compound (II) and the vinyl pyrrolidone/vinyl acetate copolymer were weighed in a ratio of 1:4 and uniformly mixed (hereinafter referred to as a comparison preparation 1).

Preparation Example 25

The isoxazoline compound (III) and the vinyl pyrrolidone/vinyl acetate copolymer were weighed in a ratio of 1:4 and uniformly mixed (hereinafter referred to as a comparison preparation 2).

Preparation Example 26

The isoxazoline compound (IV) and the vinyl pyrrolidone/vinyl acetate copolymer were weighed in a ratio of 1:4 and uniformly mixed (hereinafter referred to as a comparison preparation 3).

Preparation Example 27

The isoxazoline compound (V) and the vinyl pyrrolidone/vinyl acetate copolymer were weighed in a ratio of 1:4 and uniformly mixed (hereinafter referred to as a comparison preparation 4).

The effects obtained by the composition of the present invention and by the method of the present invention will be explained in detail below by way of test examples.

Test Example 1

Measurement of Powder X-Ray Diffractions

The powder X-ray diffractions of the compositions A, G and comparison formulation 1 were measured.

In the results of the measurement of the comparison preparation 1, as shown in FIG. 1, diffraction peaks derived from the crystal of the isoxazoline compound and/or a diffraction peak derived from the crystal of the polymer compound were observed.

Figure 2:
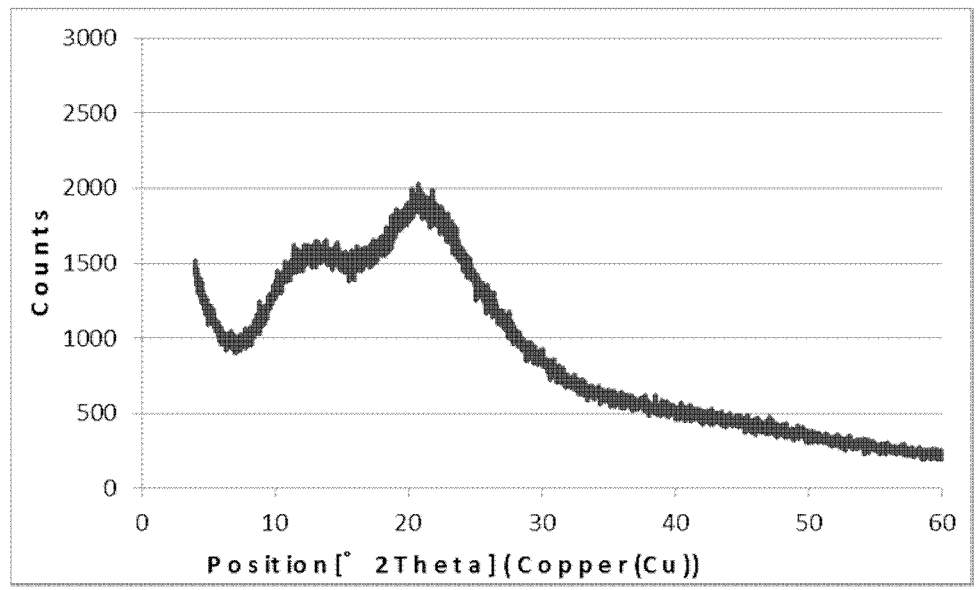
FIG. 2 is the powder X-ray diffraction of the Composition A.
Figure 3:
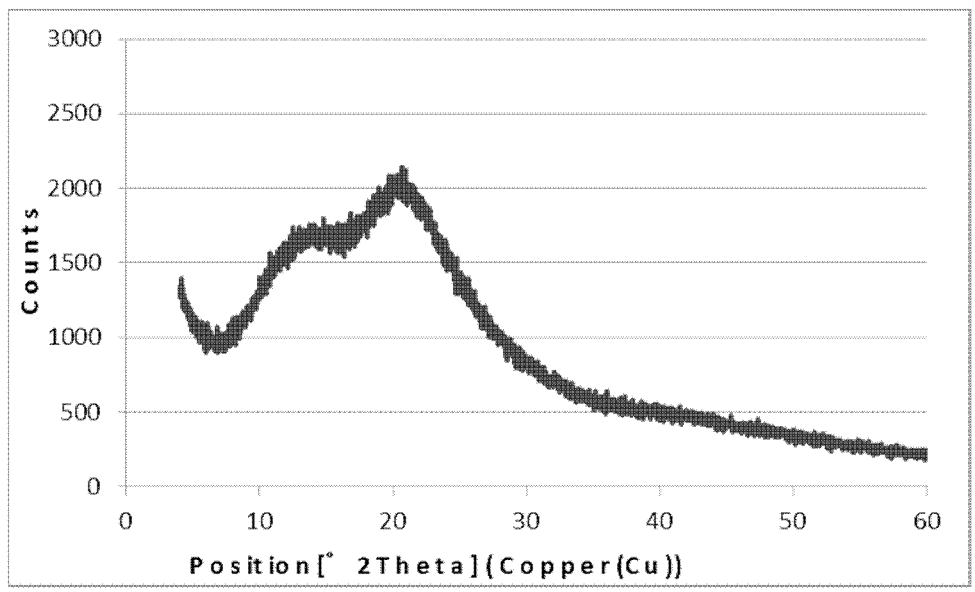
FIG. 3 is the powder X-ray diffraction of the composition G.

In the results of measurement of the composition A and G, as shown in FIGS. 2 and 3, the diffraction peaks derived from the crystal which were observed in the results of the measurement of the simply mixed sample, the comparison preparation 1, were not substantially observed. That is, the compositions A and G were each the composition of the present invention.

Test Example 2

Solubility Test in Fasted State Simulated Intestinal Fluid (FeSSIF)

20.20 g of NaOH, 43.25 g of glacial acetic acid, and 59.37 g of NaCl were dissolved in 4.9 L of deionized water in a 5 L measuring flask. The solution was adjusted to pH 5.0 by using 1 N NaOH and 1 N HCl and then, water was added to the solution to be a volume of 5 L (hereinafter, referred to as a FeSSF buffer). 11.2 g of SIF powder (trade name, manufactured by Phares Drug Delivery Co., Ltd.) was added into a 1 L measuring flask and dissolved to obtain a transparent and FeSSIF with the above FeSSIF buffer to 0.5 L at ambient temperature.

45 mL of the FeSSIF was added into a glass vial kept at 25° C. Each of the compositions (comparison preparations 1 to 4, compositions A, B, C, D, E, F, G, P, Q, R, S, U, V, and W) was added into a glass vial and then was stirred for 180 min. In this case, each composition was added such that the amount of the isoxazoline compound in the composition was 10 mg. The concentration of the isoxazoline compound in the stirred solution was measured by HPLC to find the solubility of the compound in FeSSIF. The results are shown in Table 1.

TABLE 1

| | Preparation formulation | Production method | Solubility (ppm) |
|---|---|---|---|
| Comparison plot 1 | comparison preparation 1 | Simple mixture | 33.32 |
| Comparison plot 2 | comparison preparation 2 | Simple mixture | 16.60 |
| Comparison plot 3 | comparison preparation 3 | Simple mixture | 28.79 |

TABLE 1-continued

| | Preparation formulation | Production method | Solubility (ppm) |
|---|---|---|---|
| Comparison plot 4 | comparison preparation 4 | Simple mixture | 138.21 |
| Test plot 1 | Composition P | Melt method | 180.70 |
| Test plot 2 | Composition Q | Melt method | 195.61 |
| Test plot 3 | Composition R | Melt method | 224.94 |
| Test plot 4 | Composition S | Melt method | 247.72 |
| Test plot 5 | Composition A | Melt method | 231.29 |
| Test plot 6 | Composition G | solvent method | 210.04 |
| Test plot 7 | Composition U | Melt method | 200.66 |
| Test plot 8 | Composition V | Melt method | 216.85 |
| Test plot 9 | Composition W | Melt method | 207.91 |
| Test plot 10 | Composition B | Melt method | 196.35 |
| Test plot 11 | Composition C | Melt method | 153.71 |
| Test plot 12 | Composition D | Melt method | 106.00 |
| Test plot 13 | Composition E | Melt method | 205.00 |
| Test plot 14 | Composition F | Melt method | 213.14 |

Test Example 3

Oral Administration Against Rabbit (Strain:Japanese White)—Infested Ticks

Preparation 50 parts by weight of each of the compositions A, B, C, D, E, F, G, J, L, N, and O, 9 parts by weight of microcrystalline cellulose, 20 parts by weight of low-substituted hydroxypropyl cellulose, 20 parts by weight of light anhydrous silica, and 1 part by weight of magnesium stearate were mixed and tabletted to prepare tablets.

Comparison plot 5: 20 parts by weight of the isoxazoline compound (II), 33 parts by weight of lactose, 14.2 parts by weight of microcrystalline cellulose, 11.8 parts by weight of low-substituted hydroxypropyl cellulose, 20 parts by weight of light anhydrous silica, and 1 part by weight of magnesium stearate were uniformly mixed in a mortar and the mixed powder was tabletted to prepare a tablet.

Comparison plot 6: 20 parts by weight of the isoxazoline compound (II), 40 parts by weight of hydroxypropylmethyl cellulose, 9 parts by weight of microcrystalline cellulose, 20 parts by weight of low-substituted hydroxypropyl cellulose, 20 parts by weight of light anhydrous silica, and 1 part by weight of magnesium stearate were uniformly mixed in a mortar at ambient temperature and the mixed powder was tabletted to prepare a tablet.

The following materials were excipients for tablets. Microcrystalline cellulose (trade name: Cellulose, microcrystalline, Alfa Aesar)
Low-substituted hydroxypropyl cellulose (trade name: L-HPC (LH-21), Shin-Etsu Chemical Co., Ltd.)
Light anhydrous silica (trade name: Carplex #80, manufactured by Evonik Degussa Japan Co., Ltd.)
Magnesium stearate (trade name: Magnesium Stearate, manufactured by Wako Pure Chemical Industries, Ltd.)

TABLE 2

| | Test plot 15 | Test plot 16 | Test plot 17 | Test plot 18 | Test plot 19 |
|---|---|---|---|---|---|
| Production method | Melt method | Melt method | Melt method | Melt method | Melt method |
| Dosage form | Tablet | Tablet | Tablet | Tablet | Tablet |
| Composition A | 50 wt % | — | — | — | — |
| Composition B | — | 50 wt % | — | — | — |
| Composition C | — | — | 50 wt % | — | — |
| Composition D | — | — | — | 50 wt % | — |

TABLE 2-continued

| | | | | | |
|---|---|---|---|---|---|
| Composition E | — | — | — | — | 50 wt %- |
| Microcrystalline cellulose | 9 wt % | 9 wt % | 9 wt % | 9 wt % | 9 wt % |
| Low-substituted hydroxypropyl cellulose | 20 wt % | 20 wt % | 20 wt % | 20 wt % | 20 wt % |
| Light anhydrous silica | 20 wt % | 20 wt % | 20 wt % | 20 wt % | 20 wt % |
| Magnesium stearate | 1 wt % | 1 wt % | 1 wt % | 1 wt % | 1 wt % |

| | Test plot 20 | Test plot 21 | Test plot 22 | Test plot 23 | Test plot 24 |
|---|---|---|---|---|---|
| Production method | Melt method | Solvent method | Solvent method | Solvent method | Solvent method |
| Dosage form | Tablet | Tablet | Tablet | Tablet | Tablet |
| Composition F | 50 wt % | — | — | — | — |
| Composition G | — | 50 wt % | — | — | — |
| Composition J | — | — | 50 wt % | — | — |
| Composition L | — | — | — | 50 wt % | — |
| Composition N | — | — | — | — | 50 wt % |
| Microcrystalline cellulose | 9 wt % | 9 wt % | 9 wt % | 9 wt % | 9 wt % |
| Low-substituted hydroxypropyl cellulose | 20 wt % | 20 wt % | 20 wt % | 20 wt % | 20 wt % |
| Light anhydrous silica | 20 wt % | 20 wt % | 20 wt % | 20 wt % | 20 wt % |
| Magnesium stearate | 1 wt % | 1 wt % | 1 wt % | 1 wt % | 1 wt % |

| | Test plot 25 | Comparison plot 5 | Comparison plot 6 |
|---|---|---|---|
| Production method | Solvent method | — | (Simple mixing) |
| Dosage form | Tablet | Tablet | Tablet |
| Composition O | 50 wt % | | |
| Isoxazoline compound (II) | | 20 wt % | 10 wt % |
| Hydroxypropylmethyl cellulose | — | — | 40 wt % |
| Lactose | — | 33 wt % | — |
| Microcrystalline cellulose | 9 wt % | 14.2 wt % | 9 wt % |
| Low-substituted hydroxypropyl cellulose | 20 wt % | 11.8 wt % | 20 wt % |
| Light anhydrous silica | 20 wt % | 20 wt % | 20 wt % |
| Magnesium stearate | 1 wt % | 1 wt % | 1 wt % |

(Animal Test)

Rabbits (Japanese white color species) were each inoculated with 50 ticks (*Haemaphysalis longicornis*, young ticks) on the day before the administration. The tablets prepared above were each orally administered to each rabbit, such that the amount of the isoxazoline compound was 20 mg/kg per weight (kg) of the rabbit (Test plots 15 to 25, Comparison plot 5 to 6). Nothing was administered to a control group.

The number of living ticks parasitic on the rabbit was examined on the second day after the administration of the isoxazoline compound. The control rate was calculated using the following calculation formula.

Control rate on the $x$th day (%)=(1−Average number of parasites of test plot or Comparison plot on the $x$th day/Average number of parasites of control group on the $x$th day)×100

TABLE 3

| | Control rate of ticks (%) On the second day after the administration |
|---|---|
| Test plot 15 | 100 |
| Test plot 16 | 96 |
| Test plot 17 | 95 |
| Test plot 18 | 100 |
| Test plot 19 | 98 |
| Test plot 20 | 99 |
| Test plot 21 | 100 |
| Test plot 22 | 100 |
| Test plot 23 | 100 |
| Test plot 24 | 100 |
| Test plot 25 | 99 |
| Comparison plot 5 | 80 |
| Comparison plot 6 | 78 |

Test Example 4

Oral Administration Against Mouse(Strain:Ddy)—Infested Ticks (*Haemaphysalis longicornis*)

Mice (its species will be described later) were each inoculated with 20 ticks (*Haemaphysalis longicornis*, young ticks) on the day before the administration. The compositions Q, R, and S were each suspended in deionized water and orally administered to each mouse. The amount of the isoxazoline compound was shown in the following tables. Nothing was administered to a control group.

The number of living ticks parasitic on the mouse was examined on the second day after the administration of the composition. All parasitic ticks were removed from the mouse when the observation was finished on the second day after the administration. The control rate was calculated using the calculation formula described in Test Example 3.

TABLE 4

| | Preparation formulation | Production method | Dose (mg/kg) | Control rate (%) |
|---|---|---|---|---|
| Comparison plot 7 | comparison formulation 1 | Simple mixture | 15 | 70 |
| Comparison plot 8 | comparison preparation 2 | Simple mixture | 5 | 17 |
| Comparison plot 9 | comparison preparation 3 | Simple mixture | 0.2 | 1 |
| Comparison plot 10 | comparison preparation 4 | Simple mixture | 0.6 | 6.9 |
| Test plot 26 | Composition Q | Melt method | 15 | 100 |
| Test plot 27 | Composition R | Melt method | 15 | 100 |
| Test plot 28 | Composition S | Melt method | 15 | 100 |
| Test plot 29 | Composition A | Melt method | 15 | 96 |
| Test plot 30 | Composition U | Melt method | 5 | 72 |
| Test plot 31 | Composition V | Melt method | 0.2 | 100 |
| Test plot 32 | Composition W | Melt method | 0.6 | 92 |

Test Example 5

Oral Administration Against Dog-Infested Ticks (*Haemaphysalis longicornis*, Young Ticks)

Preparation 50 parts by weight of the composition H, 9 parts by weight of microcrystalline cellulose, 20 parts by weight of low-substituted hydroxypropyl cellulose, 20 parts by weight of light anhydrous silica, and 1 part by weight of magnesium stearate were mixed and tabletted to prepare a test plot 34 preparation. The composition H and isoxazoline compound (II) were filled in a hard gelatin capsule (manufactured by Qualicaps Co., Ltd., hereinafter referred to as "Gel-Cap") to prepare a test plot 35 preparation and comparison plot 11 preparation.
(Animal Test)

Each Dog (beagles) was infested with 50 ticks (Rhipicephalussanguineus, adult ticks) on the day before the administration.

The test plot 34 preparation, the test plot 35 preparation and comparison plot 11 preparation were each orally administered to each dog such that the amount of the isoxazoline compound was 20 mg/kg per weight (kg) of the dog. Nothing was administered to a control group.

The number of living ticks parasitic on the dog was examined on the second day after the preparation was administered. All parasitic ticks were removed from the dog when the observation was finished on the second day after the administration.

Further, the each dog was infested again with 50 ticks on the 14th day after administering the isoxazoline compound. The number of living ticks parasitic on the dog was examined on the 15th day after administering the isoxazoline compound, and all parasitic ticks were removed from the dog when the observation was finished on the 15th day.

The control rate was calculated using the following calculation formula.

Control rate on the $x$th day (%)=(1−Average number of parasites of test plot or Comparison plot on the $x$th day/Average number of parasites of a control group on the $x$th day)×100

TABLE 5

| | Test plot 34 | Test plot 35 | Comparison plot 11 |
|---|---|---|---|
| Production method | Solvent method | Solvent method | — |
| Dosage form | Tablet | Gel-Cap | Gel-Cap |
| Composition H | 50 wt % | 100 wt % | |
| Isoxazoline compound (II) | | | 100 wt % |
| Microcrystalline cellulose | 9 wt % | | — |
| Low-substituted hydroxypropyl cellulose | 20 wt % | | — |
| Light anhydrous silica | 20 wt % | | — |
| Magnesium stearate | 1 wt % | | — |

TABLE 6

| | Control rate of ticks (%) | |
|---|---|---|
| | On the second day after the administration | On the 15th day after the administration |
| Test plot 34 | 100 | 90 |
| Test plot 35 | 97 | 97 |
| Comparison plot 11 | 85 | 56 |

Test Example 6

Oral Administration Test Against *Haemaphysalis Longicornis* Parasitic on Dogs

Preparation 50 parts by weight of the composition I, 9 parts by weight of microcrystalline cellulose, 20 parts by weight of low-substituted hydroxypropyl cellulose, 20 parts by weight of light anhydrous silica, and 1 part by weight of magnesium stearate were mixed and tabletted to prepare a test plot 36 preparation.

50 parts by weight of the composition K, 9 parts by weight of microcrystalline cellulose, 20 parts by weight of low-substituted hydroxypropyl cellulose, 20 parts by weight of light anhydrous silica, and 1 part by weight of magnesium stearate were mixed and tabletted to prepare a test plot 37 preparation.

50 parts by weight of the composition M, 9 parts by weight of microcrystalline cellulose, 20 parts by weight of low-substituted hydroxypropyl cellulose, 20 parts by weight of light anhydrous silica, and 1 part by weight of magnesium stearate were mixed and tabletted to prepare a test plot 38 preparation.

(Animal Test)

The aforementioned test plots 36 to 38 preparations were each orally administered to each dog, such that the amount of the isoxazoline compound was 20 mg/kg per weight (kg) of the dog. Nothing was administered to dogs of a control group.

The dogs of the test plot, Comparison plot and control group were each infested with 100 ticks (*Haemaphysalis longicornis*, adult ticks) on the 14th day after the test preparation was administered. The number of living ticks parasitic on the dog was examined on the 15th day after the isoxazoline compound was administered. The control rate was calculated using the aforementioned calculation formula.

TABLE 7

| | Test plot 36 | Test plot 37 | Test plot 38 |
|---|---|---|---|
| Production method | Solvent method | Solvent method | Solvent method |
| Dosage form | Tablet | Tablet | Tablet |
| Composition I | 50 wt % | — | — |
| Composition K | — | 50 wt % | — |
| Composition M | — | — | 50 wt % |
| Microcrystalline cellulose | 9 wt % | 9 wt % | 9 wt % |
| Low-substituted hydroxypropyl cellulose | 20 wt % | 20 wt % | 20 wt % |
| Light anhydrous silica | 20 wt % | 20 wt % | 20 wt % |
| Magnesium stearate | 1 wt % | 1 wt % | 1 wt % |

TABLE 8

| | Control rate of ticks (%) On the 15th day after the administration |
|---|---|
| Test plot 36 | 100 |
| Test plot 37 | 100 |
| Test plot 38 | 100 |

Test Example 7

Oral Administration Against Dog-Infested Cat Fleas (*Ctenocephalides felis*)

(Animal Test)

The test plots 34 and 35 preparations prepared in Test Example 5 were each orally administered to each dog, such that the amount of the isoxazoline compound was 20 mg/kg per weight (kg) of the dog. Nothing was administered to dogs of a control group.

The dogs of the test plot, Comparison plot and the control group were each infested with 50 fleas (*Ctenocephalides felis*, adult fleas) on the first day after administering the test preparation. The number of living fleas parasitic on the dog was examined on the second day after the administration, and all parasitic fleas were removed from the dog when the observation was finished.

Further, the dogs were each infested again with 50 fleas on the 28th day after administering the test preparation. The number of living fleas parasitic on the dog was examined on the 30th day after the administration. The control rate was calculated using the aforementioned calculation formula.

TABLE 9

| | | Control rate of cat fleas (%) | |
|---|---|---|---|
| | Administered preparation | On the second day after the administration | On the 30th day after the administration |
| Test plot 39 | Test plot 34 preparation | 100 | 100 |
| Test plot 40 | Test plot 35 preparation | 100 | 99 |

INDUSTRIAL APPLICABILITY

The composition of the present invention has an excellent control effect on animal ectoparasites and is therefore useful.

The invention claimed is:

1. A composition comprising an isoxazoline compound represented by the following formula (I), the isoxazoline compound being dispersed in a solid vehicle of at least one polymer compound selected from cellulose polymers and vinyl polymers, wherein a diffraction peak of at least one of a crystal of the isoxazoline compound and a crystal of the at least one polymer compound is substantially not observed in a powder X-ray diffraction pattern of the composition, or wherein the diffraction peak is reduced compared to a diffraction peak area observed in a powder X-ray diffraction pattern of crystals in a simple solid state mixture of the isoxazoline compound and the at least one polymer compound:

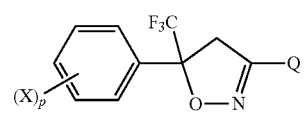
(I)

wherein X represents a halogen atom or a C1-C3 haloalkyl group, p denotes an integer from 0 to 5; and Q represents a group selected from the following Q1 to Q8:

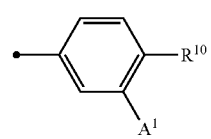
Q1

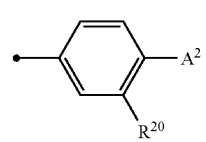
Q2

-continued

[Structures Q3–Q8 shown, including: a phenyl-azetidine with R⁴¹ and R⁴⁰ substituents bonded to A⁴; an indane with A⁵; a naphthalene with A⁶; an indolizine-type bicyclic with OH and T; a thiophene/furan-like ring with T² , A⁸, R⁸⁰; and a spiro isobenzofuran-azetidine with A⁹]

[Bracketed set of groups including: pyridyl-R³⁶, pyrimidinyl-R³⁶, pyrazinyl-R³⁶, tetrahydrofuranyl, thiolanyl-S(O), thietanyl-S(O)ₘ (three variants), dithiolanyl, 1,2-oxathiolanyl-S(O)ₘ, isothiazolidinyl-N-R³, isoxazolidinone-N-R³⁷ (two variants)]

wherein m denotes a number of 0, or 2, $R^{36}$ represents a hydrogen atom, a chlorine atom, or a cyano group, and $R^{37}$ represents a hydrogen atom, a C1-C6 alkyl group, or a C1-C6 haloalkyl group, $R^{22}$ represents a hydrogen atom, a (C1-C6 alkyl)carbonyl group or a (C1-C6 alkoxy)carbonyl group, $R^{23}$ represents a C1-C6 alkyl group, a C1-C6 haloalkyl group, or a (C1-C6 alkoxy)C1-C6 alkyl group, $R^{24}$ represents a hydrogen atom or a C1-C3 alkyl group, $R^{25}$ represents a hydrogen atom or a C1-C3 alkyl group, $R^{26}$ represents a phenyl group, $R^{27}$ represents a hydrogen atom or a C1-C3 alkyl group, $R^{28}$ represents a C1-C3 alkoxy group, $R^{29}$ represents a C1-C6 alkyl group, a C1-C6 haloalkyl group, a C3-C6 cycloalkyl group, a (C3-C6 cycloalkyl)C1-C6 alkyl group, a (C1-C6 alkoxy)C1-C6 alkyl group, or a C1-C6 alkoxy group, $R^{30}$ represents a hydrogen atom or a C1-C3 alkyl group, $R^{31}$ represents a hydrogen atom or a C1-C3 alkyl group, $R^{32}$ represents a hydrogen atom, a C1-C6 alkyl group, or a C1-C6 haloalkyl group, $R^{33}$ represents a hydrogen atom, a cyano group, a C1-C3 alkyl group, a C1-C3 alkoxy group, or a (C1-C3 alkyl)carbonyl group, $R^{34}$ represents a C1-C6 alkyl group, a C1-C6 haloalkyl group, or a (C3-C6 cycloalkyl)C1-C6 alkyl group, and $R^{35}$ represents a hydrogen atom, a C1-C6 alkyl group, or a C1-C6 haloalkyl group;

$A^{4}$ represents $R^{42}$—C(=O)— or $R^{42}$—NH—C(=O)—, $R^{40}$ represents a hydrogen atom, a halogen atom a nitro group, an amino group, an acetylamino group, or a C1-C3 alkyl group, and $R^{41}$ represents a hydrogen atom, a fluorine atom, or a hydroxyl group, where $R^{42}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl) C1-C6 alkyl group, or a (C1-C6 alkylsulfonyl)C1-C6 alkyl group;

wherein;

$A^{1}$ represents $R^{11}$—C(=O)—N($R^{12}$)—N($R^{13}$)—, $R^{11}$—C(=O)—N($R^{12}$)—CH₂—, or $R^{11}$—C(=O)—N($R^{12}$)— and $R^{10}$ represents a hydrogen atom, a halogen atom, or a C1-C3 alkyl group, where $R^{11}$ represents a C1-C6 alkyl group, a C1-C6 haloalkyl group, a C3-C6 cycloalkyl group, or a (C1-C6 alkoxy)C1-C6 alkyl group, $R^{12}$ represents a hydrogen atom or a methyl group, and $R^{13}$ represents a hydrogen atom or a methyl group;

$A^{2}$ represents $R^{21}$—N($R^{22}$)—C(=O)—, $R^{23}$—N($R^{24}$)—C(=O)—CH($R^{25}$)—N($R^{22}$)—C(=O)—, $R^{26}$—N($R^{27}$)—N($R^{22}$)—C(=O)—, $R^{28}$—N=CH—N($R^{22}$)—C(=O)—, $R^{29}$—C(=O)—N($R^{30}$)—CH($R^{31}$)—, $R^{32}$—O—N=C($R^{33}$)—, $R^{34}$—NH—C(=O)—CH₂O—N=C($R^{33}$)—, $R^{34}$—NH—C(=O)—NH—N=C($R^{33}$)—, or $R^{35}$—NH—C(=NH)—NH—N=C($R^{33}$)—, and $R^{20}$ represents a hydrogen atom, a halogen atom, a nitro group, an amino group, an acetylamino group, or a C1-C3 alkyl group, where $R^{21}$ represents a C1-C6 alkyl group, a C1-C6 haloalkyl group, a (hydroxy)C1-C6 alkyl group, a (C1-C6 alkoxy)C1-C6 alkyl group, a (C1-C6 alkylthio)C1-C6 alkyl group, or one heterocyclic group selected from the following group;

A⁵ represents R⁵¹—N(R⁵²)—, R⁵³—C(O)—N(R⁵²)—, R⁵¹—N(R⁵²)—C(=O)—N(R⁵²)—, R⁵¹—O—C(=O)—N(R⁵²)—, or R⁵³—C(=O)—, where
R⁵¹ represents a C1-C6 alkyl group, a C1-C6 haloalkyl group, or a C3-C6 cycloalkyl group,
R⁵² represents a hydrogen atom or a C1-C3 alkyl group, and
R⁵³ represents a C1-C6 alkyl group, a C1-C6 haloalkyl group, a C3-C6 cycloalkyl group, a (hydroxy)C1-C6 alkyl group, or a (C1-C6 alkoxy)C1-C6 alkyl group;
A⁶ represents R⁶¹—N(R⁶²)—C(=O)— or R⁶³—N(R⁶⁴)—C(=O)—CH(R⁶⁵)—N(R⁶²)—C(=O)—, where
R⁶¹ represents a C1-C6 alkyl group, a C1-C6 haloalkyl group, a (hydroxy)C1-C6 alkyl group, a (C1-C6 alkoxy)C1-C6 alkyl group, or a C1-C6 alkylthio)C1-C6 alkyl group,
R⁶² represents a hydrogen atom, a (C1-C6 alkyl)carbonyl group or a (C1-C6 alkoxy)carbonyl group,
R⁶³ represents a C1-C6 alkyl group, a C1-C6 haloalkyl group, or a (C1-C6 alkoxy C1-C6 alkyl group,
R⁶⁴ represents a hydro en atom or a C1-C6 alkyl group, and
R⁶⁵ represents a hydrogen atom;
A⁷ represents R⁷¹—N(R⁷²)—C(=O)— or R⁷³—N(R⁷⁴)—C(=O)—CH(R⁷⁵)—N(R⁷)—C(=O)—, and
T represents a nitrogen atom or CR⁷⁶, where
R⁷¹ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio)C1-C6 alkyl group,
R⁷² represents a hydrogen atom, a C1-C6 alkyl)carbonyl group, or a (C1-C6 alkoxy)carbonyl group,
R⁷³ represents a C1-C6 alkyl group, a C1-C6 haloalkyl group, or a (C1-C6 alkoxy)C1-C6 alkyl group,
R⁷⁴ represents a hydrogen atom or a C1-C6 alkyl group,
R⁷⁵ represents a hydrogen atom or a C1-C6 alkyl group, and
R⁷⁶ represents a hydrogen atom or a C1-C3 alkyl group;
T² represents —CH₂=CH₂—, an oxygen atom, or a sulfur atom;
A⁸ represents R¹¹—C(=O)—N(R¹²)—N(R¹³) or R¹¹—C(=O)—N(R¹²)—CH₂— and
R⁸⁰ represents a hydrogen atom, a halogen atom, or a C1-C3 alkyl group; and
A⁹ represents R⁹²—C(=O)— or R⁹²—NH—C(=O)—, where
R⁹² represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group.

2. The composition according to claim 1, wherein the ratio by weight of the isoxazoline compound to the polymer compound is 1:0.1 to 1:100.

3. The composition according to claim 1, wherein the polymer compound is one or more polymer compounds selected from the group consisting of a vinyl pyrrolidone/vinyl acetate copolymer, polyvinyl pyrrolidone, dimethylaminoethyl methacrylate/butyl methacrylate/methyl methacrylate copolymer, hydroxypropylmethyl cellulose acetate succinate, hydroxypropylmethyl cellulose phthalate and hydroxypropylmethyl cellulose.

4. The composition according to claim 1, wherein the isoxazoline compound is one or more compounds selected from compounds represented by the following formulae (II) to (V):

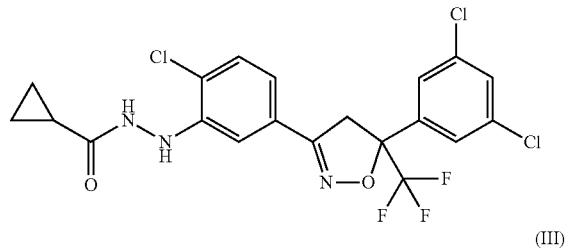
(II)

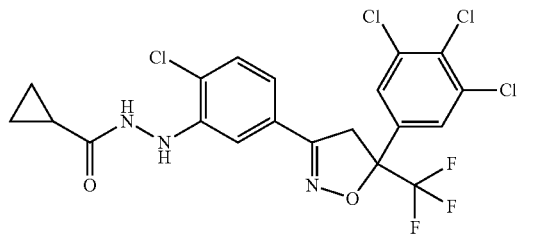
(III)

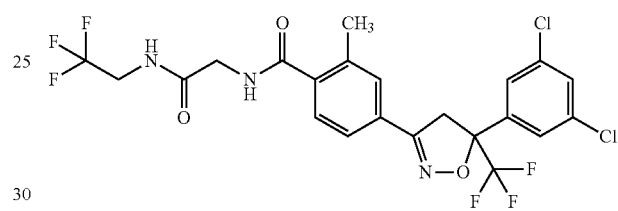
(IV)

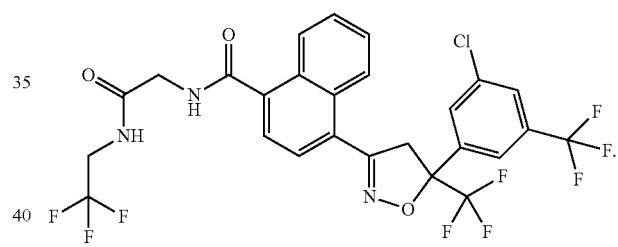
(V)

5. The composition according to claim 1, wherein the isoxazoline compound is compound (V):

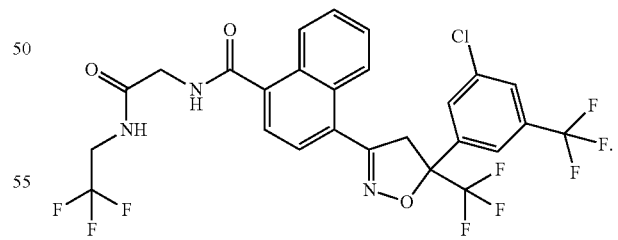
(V)

6. An animal ectoparasiticide produced using the composition as claimed in claim 1.

7. A method for controlling ectoparasites, the method comprising orally administering the composition as claimed in claim 1 to a host animal.

8. A method for controlling ectoparasites, the method comprising orally administering the animal ectoparasiticide as claimed in claim 6 to a host animal.

9. The method for controlling ectoparasites according to claim 7, wherein the ectoparasite to be controlled is an ectoparasite belonging to order Siphonaptera, order Anoplura, or order Acarina.

10. The method for controlling ectoparasites according to claim 8, wherein the ectoparasite to be controlled is an ectoparasite belonging to order Siphonaptera, order Anoplura, or order Acarina.

11. The method for controlling ectoparasites according to claim 7, wherein the host animal is a livestock animal or a pet.

12. The method for controlling ectoparasites according to claim 8, wherein the host animal is a livestock animal or a pet.

13. The method for controlling ectoparasites according to claim 7, wherein the host animal is a dog, a cat, a horse, or a rabbit.

14. The method for controlling ectoparasites according to claim 8, wherein the host animal is a dog, a cat, a horse, or a rabbit.

15. A method for producing a composition, the method comprising a step of kneading a mixture of an isoxazoline compound represented by the formula (I) and at least one polymer compound selected from cellulose polymers and vinyl polymers at a temperature equal to or higher than the melting point of the isoxazoline compound and equal to or higher than the temperature at which the at least one polymer compound melts, for at least 3 minutes and a step of, then, cooling the kneaded mixture to a temperature less than the melting point of the isoxazoline compound and less than the glass transition temperature of the at least one polymer compound:

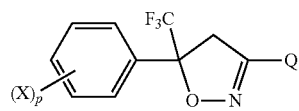
(I)

wherein X represents a halogen atom or a C1-C3 haloalkyl group p denotes an integer from 0 to 5; and
Q represents a group elected from the following Q1 to Q8:

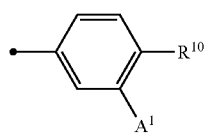
Q1

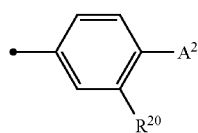
Q2

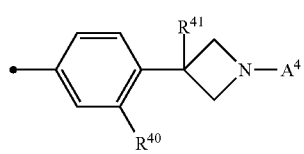
Q3

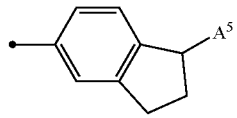
Q4

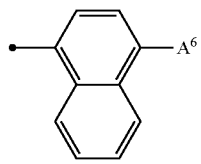
Q5

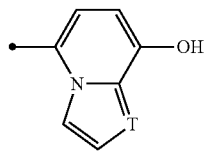
Q6

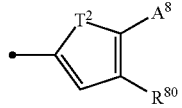
Q7

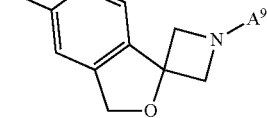
Q8 wherein;

$A^1$ represents $R^{11}$—C(=O)—N($R^{12}$)—N($R^{13}$)—, $R^{11}$—C(=O)—N($R^{12}$)—CH$_2$—, or $R^{11}$—C(=O)—N($R^{12}$)— and $R^{10}$ represents a hydrogen atom, a halogen atom, or a C1-C3 alkyl group, where $R^{11}$ represents a C1-C6 alkyl group, a C1-C6 haloalkyl group, a C3-C6 cycloalkyl group, or a (C1-C6 alkoxy) C1-C6 alkyl group, $R^{12}$ represents a hydrogen atom or a methyl group, and $R^{13}$ represents a hydrogen atom or a methyl group;

$A^2$ represents $R^{21}$—N($R^{22}$)—C(=O)—, $R^{23}$—N($R^{24}$) C(=O)—CH($R^{25}$)—N($R^{22}$)—C(=O)—, $R^{26}$—N ($R^{27}$)—N($R^{22}$)—C(=O)—, $R^{28}$—N=CH—N ($R^{22}$)—C(=O)—, $R^{29}$—C(=O)N($R^{30}$)—CH ($R^{31}$)—, $R^{32}$—O—N=C($R^{33}$)—, $R^{34}$—NH—C (=O)—CH$_2$O—N=C($R^{33}$)—, $R^{34}$—NH—C (=O)—NH—N=C($R^{33}$)—, or $R^{35}$—NH—C (=NH)—NH—N=C($R^{33}$)—, and $R^{20}$ represents a hydrogen atom, a halogen atom a nitro group, an amino group, an acetylamino group or a C1-C3 alkyl group, where $R^{21}$ represents a C1-C6 alkyl group, a C1-C6 haloalkyl group, a (hydroxy)C1-C6 alkyl group, a (C1-C6 alkoxy) C1-C6 alkyl group, a (C1-C6 alkylthio)C1-C6 alkyl group, or one heterocyclic group selected from the following group;

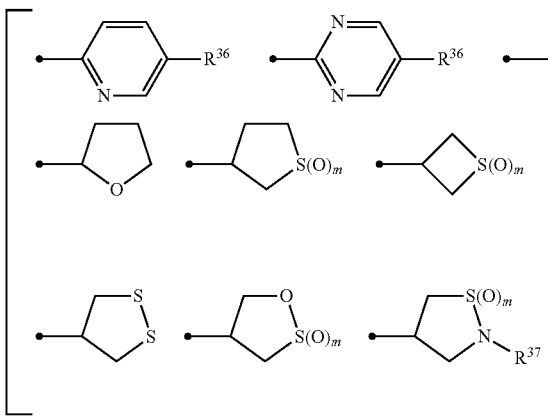

wherein m denotes a number of 0, 1 or 2, $R^{36}$ represents a hydrogen atom, a chlorine atom, or a cyano group, and $R^{37}$ represents a hydrogen atom, a C1-C6 alkyl group, or a C1-C6 haloalkyl group, $R^{22}$ represents a hydrogen atom, a (C1-C6 alkyl)carbonyl group or a (C1-C6 alkoxy)carbonyl group, $R^{23}$ represents a C1-C6 alkyl group, a C1-C6 haloalkyl group, or a (C1-C6 alkoxy)C1-C6 alkyl group, $R^{24}$ represents a hydrogen atom or a C1-C3 alkyl group, $R^{25}$ represents a hydrogen atom or a C1-C3 alkyl group, $R^{26}$ represents a phenyl group, $R^{27}$ represents a hydrogen atom or a C1-C3 alkyl group, $R^{28}$ represents a C1-C3 alkoxy group, $R^{29}$ represents a C1-C6 alkyl group, a C1-C6 haloalkyl group, a C1-C6 cycloalkyl group, a (C3-C6 cycloalkyl)C1-C6 alkyl group, a (C1-C6 alkoxy)C1-C6 alkyl group, or a C1-C6 alkoxy group, $R^{30}$ represents a hydrogen atom or a C1-C3 alkyl group, $R^{31}$ represents a hydrogen atom or a C1-C3 alkyl group, $R^{32}$ represents a hydrogen atom, a C1-C6 alkyl group, or a C1-C6 haloalkyl group, $R^{33}$ represents a hydrogen atom, a cyano group, a C1-C3 alkyl group, a C1-C3 alkoxy group, or a (C1-C3 alkyl)carbonyl group, $R^{34}$ represents a C1-C6 alkyl group, a C1-C6 haloalkyl group, or a (C3-C6 cycloalkyl)C1-C6 alkyl group, and $R^{35}$ represents a hydrogen atom, a C1-C6 alkyl group, or a C1-C6 haloalkyl group;

$A^4$ represents $R^{42}$—C(=O)— or $R^{42}$—NH—C(=O)—, $R^{40}$ represents a hydrogen atom, a halogen atom, a nitro group an amino group, an acetylamino group, or a C1-C3 alkyl group, and $R^{41}$ represents a hydrogen atom, a fluorine atom, or a hydroxyl group, where $R^{42}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group a (C1-C6 alkylthio)C1-C6 alkyl group, a (C1-C6 alkylsulfinyl)C1-C6 alkyl group, or a (C1-C6 alkylsulfonyl)C1-C6 alkyl group;

$A^5$ represents $R^{51}$—N($R^{52}$)—, $R^{53}$—C(=O)—N($R^{52}$)—, $R^{51}$—N($R^{52}$)—C(=O)—N($R^{52}$)—, $R^{51}$—O—C(=O)—N($R^{52}$)—, or $R^{53}$—C(=O)—, where $R^{51}$ represents a C1-C6 alkyl group, a C1-C6 haloalkyl group or a C3-C6 cycloalkyl group, $R^{52}$ represents a hydrogen atom or a C1-C3 alkyl group, and $R^{53}$ represents a C1-C6 alkyl group, a C1-C6 haloalkyl group, a C3-C6 cycloalkyl group, a (hydroxy)C1-C6 alkyl group, or a (C1-C6 alkoxy)C1-C6 alkyl group;

$A^6$ represents $R^{61}$—N($R^{62}$)—C(=O)— or $R^{63}$—N($R^{64}$)—C(=O)—CH($R^{65}$)—N($R^{62}$)—C(=O)—, where $R^{61}$ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio)C1-C6 alkyl group, $R^{62}$ represents a hydrogen atom, a (C1-C6 alkyl)carbonyl group or a (C1-C6 alkoxy)carbonyl group, $R^{63}$ represents a C1-C6 alkyl group, a C1-C6 haloalkyl group, or a (C1-C6 alkoxy)C1-C6 alkyl group, $R^{64}$ represents a hydrogen atom or a C1-C6 alkyl group, and $R^{65}$ represents a hydrogen atom;

$A^7$ represents $R^{71}$—N($R^{72}$)C(=O)— or $R^{73}$—N($R^{74}$)—C(=O)—CH($R^{75}$)—N($R^{72}$)—C(=O)—, and T represents a nitrogen atom or $CR^{76}$, where $R^{71}$ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio C1-C6 alkyl group, $R^{72}$ represents a hydrogen atom, a (C1-C6 alkyl)carbonyl group, or a (C1-C6 alkoxy)carbonyl group, $R^{73}$ represents a C1-C6 alkyl group, a C1-C6 haloalkyl group, or a (C1-C6 alkoxy)C1-C6 alkyl group, $R^{74}$ represents a hydrogen atom or a C1-C6 alkyl group, $R^{75}$ represents a hydrogen atom or a C1-C6 alkyl group, and $R^{76}$ represents a hydrogen atom or a C1-C3 alkyl group;

$T^2$ represents —$CH_2$=$CH_2$—, an oxygen atom, or a sulfur atom;

$A^8$ represents $R^{11}$—C(=O)—N($R^{12}$)—N($R^{13}$)— or $R^{11}$—C(=O)—N($R^{12}$)—$CH_2$— and $R^{80}$ represents a hydrogen atom, a halogen atom, or a C1-C3 alkyl group; and $A^9$ represents $R^{92}$—C(=O)— or $R^{92}$—NH—C(=O)—, where $R^{92}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group.

16. A composition comprising an isoxazoline compound of formula (I), the isoxazoline compound being dispersed in a solid vehicle of at least one polymer compound selected from cellulose polymers and vinyl polymers, wherein the composition is produced according to the method of claim 15.

17. A method for producing a composition, the method comprising a step of dissolving an isoxazoline compound represented by the formula (I) and at least one polymer compound selected from cellulose polymers and vinyl polymers in a solvent to obtain a solution and a step of distilling the solvent from the solution at a temperature less than the melting point of the isoxazoline compound and less than the glass transition temperature of the at least one polymer compound:

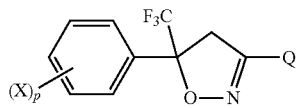
(I)

wherein X represents a halogen atom or a C1-C3 haloalkyl group, p denotes an integer from 0 to 5; and Q represents a group selected from the following Q1 to Q8:

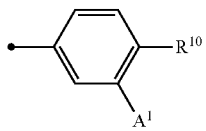
Q1

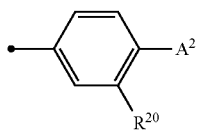
Q2

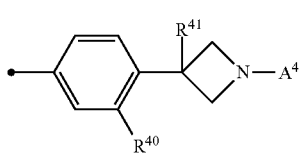
Q3

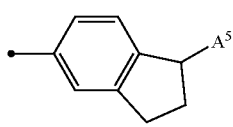
Q4

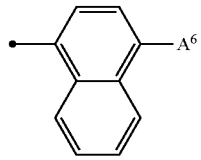
Q5

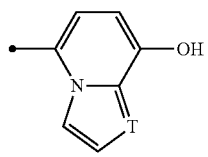
Q6

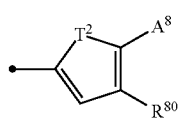
Q7

Q8 wherein;
$A^1$ represents $R^{11}$—C(=O)—N($R^{12}$)—N($R^{13}$)—, $R^{11}$—C(=O)—N($R^{12}$)—CH$_2$—, or $R^{11}$—C(=O)—N($R^{12}$)— and $R^{10}$ represents a hydrogen atom, a halogen atom, or a C1-C3 alkyl group, where $R^{11}$ represents a C1-C6 alkyl group, a C1-C6 haloalkyl group, a C3-C6 cycloalkyl group, or a (C1-C6 alkoxy) C1-C6 alkyl group, $R^{12}$ represents a hydrogen atom or a methyl group, and $R^{13}$ represents a hydrogen atom or a methyl group;

$A^2$ represents $R^{21}$—N($R^{22}$)—C(=O)—, $R^{23}$—N($R^{24}$) C(=O)—CH($R^{25}$)—N($R^{22}$)—C(=O)—, $R^{26}$—N ($R^{27}$)—N($R^{22}$)—C(=O)—, $R^{28}$—N=CH—N ($R^{22}$)—C(=O)—, $R^{29}$—C(=O)—N($R^{30}$)—CH ($R^{31}$)—, $R^{32}$—O—N=C($R^{33}$)—, $R^{34}$—NH—C (=O)—CH$_2$O—N=C($R^{33}$)—, $R^{34}$—NH—C (=O)—NH—NC($R^{33}$)—, or $R^{35}$—NH—C (=NH)—NH—N=C($R^{33}$)—, and $R^{20}$ represents a hydrogen atom, a halogen atom, a nitro group, an amino group, an acetylamino group, or a C1-C3 alkyl group, where $R^{21}$ represents a C1-C6 alkyl group, a C1-C6 haloalkyl group, a (hydroxy)C1-C6 alkyl group, a (C1-C6 alkoxy) C1-C6 alkyl group, a (C1-C6 alkylthio)C1-C6 alkyl group, or one heterocyclic group selected from the following group;

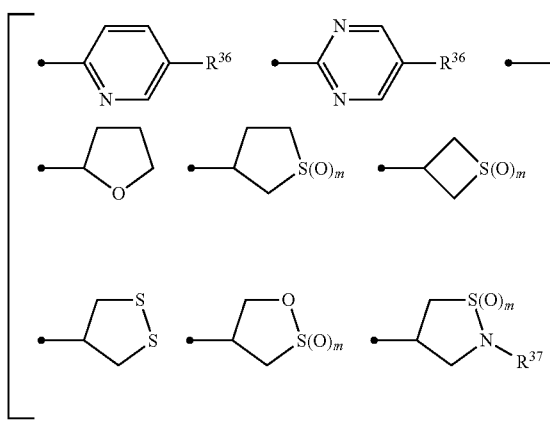

wherein m denotes a number of 0, 1 or 2, $R^{36}$ represents a hydrogen atom, a chlorine atom, or a cyano group, and $R^{37}$ represents a hydrogen atom, a C1-C6 alkyl group, or a C1-C6 haloalkyl group, $R^{22}$ represents a hydrogen atom, a (C1-C6 alkyl)carbonyl group or a (C1-C6 alkoxy)carbonyl group, $R^{23}$ represents a C1-C6 alkyl group, a C1-C6 haloalkyl group, or a (C1-C6 alkoxy)C1-C6 alkyl group, $R^{24}$ represents a hydrogen atom or a C1-C3 alkyl group, $R^{25}$ represents a hydrogen atom or a C1-C3 alkyl group, $R^{26}$ represents a phenyl group, $R^{27}$ represents a hydrogen atom or a C1-C3 alkyl group, $R^{28}$ represents a C1-C3 alkoxy group, $R^{29}$ represents a C1-C6 alkyl group, a C1-C6 haloalkyl group, a C3-C6 cycloalkyl group, a (C3-C6 cycloalkyl)C1-C6 alkyl group, a (C1-C6 alkoxy)C1-C6 alkyl group, or a C1-C6 alkoxy group, $R^{30}$ represents a hydrogen atom or a C1-C3 alkyl group, $R^{31}$ represents a hydrogen atom or a C1-C3 alkyl group, $R^{32}$ represents a hydrogen atom, a C1-C6 alkyl group, or a C1-C6 haloalkyl group, $R^{33}$ represents a hydrogen atom, a cyano group, a C1-C3 alkyl group, a C1-C3 alkoxy group, or a (C1-C3 alkyl)carbonyl group, $R^{34}$ represents a C1-C6 alkyl group, a C1-C6 haloalkyl group, or a (C3-C6 cycloalkyl)C1-C6 alkyl group, and $R^{35}$ represents a hydrogen atom, a C1-C6 alkyl group, or a C1-C6 haloalkyl group;

$A^4$ represents $R^{42}$—C(=O)— or $R^{42}$—NH—C(=O)—, $R^{40}$ represents a hydrogen atom, a halogen atom, a nitro group, an amino group, an acetylamino group, or a C1-C3 alkyl group, and $R^{41}$ represents a hydrogen atom, a fluorine atom, or a hydroxyl group, where $R^{42}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group;

$A^5$ represents $R^{51}$—N($R^{52}$)—, $R^{53}$—C(=O)—N($R^{52}$)—, $R^{51}$—N($R^{52}$)—C(=O)—N($R^{52}$)—, $R^{51}$—O—C(=O)—N($R^{52}$)—, or $R^{53}$—C(=O)—, where $R^{51}$ represents a C1-C6 alkyl group, a C1-C6 haloalkyl group, or a C3-C6 cycloalkyl group, $R^{52}$ represents a hydrogen atom or a C1-C3 alkyl group, and $R^{53}$ represents a C1-C6 alkyl group, a C1-C6 haloalkyl group, a C3-C6 cycloalkyl group, a (hydroxy)C1-C6 alkyl group, or a (C1-C6 alkoxy)C1-C6 alkyl group;

$A^6$ represents $R^{61}$—N($R^{62}$)—C(=O)— or $R^{63}$—N($R^{64}$)—C(=O)—CH($R^{65}$)—N($R^{62}$)—C(=O)—, where $R^{61}$ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio)C1-C6 alkyl group, $R^{62}$ represents a hydrogen atom, a (C1-C6 alkyl)carbonyl group or a (C1-C6 alkoxy)carbonyl group, $R^{63}$ represents a C1-C6 alkyl group, a C1-C6 haloalkyl group, or a (C1-C6 alkoxy)C1-C6 alkyl group, $R^{64}$ represents a hydrogen atom or a C1-C6 alkyl group, and $R^{65}$ represents a hydrogen atom;

$A^7$ represents $R^{71}$—N($R^{72}$)—C(=O)— or $R^{73}$—N($R^{74}$)—C(=O)—CH($R^{75}$)—N($R^{72}$)—C(=O)—, and T represents a nitrogen atom or $CR^{76}$, where $R^{71}$ represents a C1-C6 alkyl group, a C1-C6 haloalkyl group, a (hydroxy)C1-C6 alkyl group, a (C1-C6 alkoxy)C1-C6 alkyl group, or a (C1-C6 alkylthio)C1-C6 alkyl group, $R^{72}$ represents a hydrogen atom, a (C1-C6 alkyl)carbonyl group, or a (C1-C6 alkoxy)carbonyl group, $R^{73}$ represents a C1-C6 alkyl group, a C1-C6 haloalkyl group, or a (C1-C6 alkoxy)C1-C6 alkyl group, $R^{74}$ represents a hydrogen atom or a C1-C6 alkyl group, $R^{75}$ represents a hydrogen atom or a C1-C6 alkyl group, and $R^{76}$ represents a hydrogen atom or a C1-C3 alkyl group;

$T^2$ represents —$CH_2$=$CH_2$—, an oxygen atom, or a sulfur atom;

$A^8$ represents $R^{11}$—C(=O)—N($R^{12}$)—N($R^{13}$)— or $R^{11}$—C(=O)—N($R^{12}$)—$CH_2$— and $R^{80}$ represents a hydrogen atom, a halogen atom, or a C1-C3 alkyl group; and $A^9$ represents $R^{92}$—C(=O)— or $R^{92}$—NH—C(=O)—, where $R^{92}$ represents a C1-C6 alkyl group, a C1-C6 haloalkyl group, a cyano(C1-C3 alkyl) group, a C3-C6 cycloalkyl group, a (C1-C6 alkoxy)C1-C6 alkyl group, a (C1-C6 alkylthio)C1-C6 alkyl group, a (C1-C6 alkylsulfinyl)C1-C6 alkyl group, or a (C1-C6 alkylsulfonyl)C1-C6 alkyl group.

18. A composition comprising an isoxazoline compound of formula (I), the isoxazoline compound being dispersed in a solid vehicle of at least one polymer compound selected from cellulose polymers and vinyl polymers, wherein the composition is produced according to the method of claim 17.

* * * * *